US005620447A

United States Patent [19]
Smith et al.

[11] Patent Number: 5,620,447
[45] Date of Patent: Apr. 15, 1997

[54] SURGICAL INSTRUMENT

[75] Inventors: Graham Smith, Plaistow; Peter M. Cessarini, Londonderry, both of N.H.; Steven B. Woolfson, Brookline, Mass.

[73] Assignee: Smith & Nephew Dyonics Inc., Andover, Mass.

[21] Appl. No.: 534,743

[22] Filed: Sep. 27, 1995

Related U.S. Application Data

[63] Continuation of Ser. No. 200,662, Feb. 23, 1994, abandoned, which is a continuation-in-part of Ser. No. 11,364, Jan. 29, 1993, abandoned.

[51] Int. Cl.$^6$ .................................................. A61B 17/32
[52] U.S. Cl. ........................... 606/79; 606/170; 606/180; 604/22
[58] Field of Search ....................... 606/79, 80, 81, 606/82, 83, 84, 85, 150, 167, 170; 125/751, 749, 752, 753, 754, 755; 604/22

[56] References Cited

U.S. PATENT DOCUMENTS

| D. 274,096 | 5/1984 | Shutt . |
|---|---|---|
| 745,722 | 12/1903 | Freeman . |
| 1,630,239 | 5/1927 | Binkley et al. . |
| 1,636,636 | 7/1927 | Humble . |
| 2,878,809 | 3/1959 | Treace . |
| 3,342,175 | 9/1967 | Bulloch . |
| 3,618,611 | 11/1971 | Urban . |
| 3,847,154 | 11/1974 | Nordin . |
| 3,964,468 | 6/1976 | Schulz . |
| 4,020,847 | 5/1977 | Clark, III . |
| 4,167,943 | 9/1979 | Banko . |
| 4,167,944 | 9/1979 | Banko . |

(List continued on next page.)

FOREIGN PATENT DOCUMENTS

| 2074798 | 7/1992 | Canada . |
|---|---|---|
| 0393834 | 10/1990 | European Pat. Off. . |
| 0445918 | 9/1991 | European Pat. Off. . |
| 0481760 | 4/1992 | European Pat. Off. . |
| 0538984 | 4/1993 | European Pat. Off. . |
| 0609084 | 8/1994 | European Pat. Off. . |
| 0613661 | 9/1994 | European Pat. Off. . |
| 3219629 | 12/1983 | Germany . |
| 86007100.9 | 9/1986 | Germany . |
| 3828478 | 5/1989 | Germany . |
| 61-265133 | 11/1986 | Japan . |
| 1235321 | 6/1971 | United Kingdom . |
| WO93/20760 | 10/1993 | WIPO . |

OTHER PUBLICATIONS

Palmaz, J.C. et al., "Atherosclerotic Rabbit Aortas: Expandable Intraluminal Grafting", Radiology, vol. 160, No. 3, Sep. 1986, pp. 723–726.

United States Surgical Corporation Advertisement, Auto Suture™ Staplescopy™ endoscopic instruments, Journal of Laparoendoscopic Surgery, 1992.

*Primary Examiner*—Guy V. Tucker
*Attorney, Agent, or Firm*—Fish & Richardson P.C.

[57] ABSTRACT

A surgical instrument includes a first member that has an opening in its distal region for admitting tissue and that is rotatable with respect to a base from which the first member extends to allow the rotational orientation of the opening to be selectively changed with respect to the axis of the instrument. A second member is disposed within the first member to transmit force to move a cutting implement disposed at its distal end and cause it to cut tissue that is exposed to the implement through the opening. In another aspect of the invention, a surgical instrument includes a rigid member that has a bend region that angularly offsets a distal region from a proximal region mounted to a first section of a base; a surgical device extending distally from a second section of the base coaxially with the rigid member carries a surgical tool distal of the bend region, and is flexible at least in the bend region to transmit force applied at a proximal end of the surgical device through the bend region to operate the surgical tool; the first base section is rotatable with respect to the second base section, allowing the relative rotational orientation between the surgical tool and the bend region to be changed.

74 Claims, 10 Drawing Sheets

U.S. PATENT DOCUMENTS

| | | | |
|---|---|---|---|
| 4,203,444 | 5/1980 | Bonnell et al. | 604/22 |
| 4,246,902 | 1/1981 | Martinez . | |
| 4,258,716 | 3/1981 | Sutherland . | |
| 4,265,231 | 5/1981 | Scheller, Jr. et al. . | |
| 4,274,414 | 6/1981 | Johnson et al. . | |
| 4,320,761 | 3/1982 | Haddad . | |
| 4,433,687 | 2/1984 | Burke et al. . | |
| 4,440,170 | 4/1984 | Golden et al. . | |
| 4,445,509 | 5/1984 | Auth . | |
| 4,466,429 | 8/1984 | Loscher et al. . | |
| 4,483,562 | 11/1984 | Schoolman | 294/19 |
| 4,512,344 | 4/1985 | Barber . | |
| 4,517,977 | 5/1985 | Frost . | |
| 4,522,206 | 6/1985 | Whipple et al. . | |
| 4,541,423 | 9/1985 | Barber | 128/92 |
| 4,545,374 | 10/1985 | Jacobson . | |
| 4,576,772 | 3/1986 | Carpenter | 264/154 |
| 4,589,412 | 5/1986 | Kensey . | |
| 4,631,052 | 12/1986 | Kensey | 604/22 |
| 4,632,110 | 12/1986 | Sanagi . | |
| 4,644,951 | 2/1987 | Bays . | |
| 4,646,738 | 3/1987 | Trott . | |
| 4,649,919 | 3/1987 | Thimsen et al. . | |
| 4,662,371 | 5/1987 | Whipple et al. . | |
| 4,669,471 | 6/1987 | Hayashi . | |
| 4,674,501 | 6/1987 | Greenberg . | |
| 4,681,106 | 7/1987 | Kensey et al. . | |
| 4,690,140 | 9/1987 | Mecca . | |
| 4,696,667 | 9/1987 | Masch | 604/22 |
| 4,705,038 | 11/1987 | Sjostrom et al. . | |
| 4,706,655 | 11/1987 | Krauter | 128/4 |
| 4,738,256 | 4/1988 | Freeman et al. . | |
| 4,739,762 | 4/1988 | Palmaz . | |
| 4,760,848 | 8/1988 | Hasson . | |
| 4,763,669 | 8/1988 | Jaeger | 128/751 |
| 4,770,174 | 9/1988 | Luckman et al. . | |
| 4,834,729 | 5/1989 | Sjostrom . | |
| 4,842,578 | 6/1989 | Johnson et al. | 604/22 |
| 4,858,897 | 8/1989 | Irifune | 267/181 |
| 4,867,155 | 9/1989 | Isaacson . | |
| 4,880,015 | 11/1989 | Nierman | 128/751 |
| 4,945,920 | 8/1990 | Clossick | 128/751 |
| 4,950,273 | 8/1990 | Briggs | 606/113 |
| 4,982,727 | 1/1991 | Sato . | |
| 4,986,825 | 1/1991 | Bays et al. | 604/22 |
| 4,998,527 | 3/1991 | Meyer | 128/6 |
| 5,094,247 | 3/1992 | Hernandez et al. | 128/751 |
| 5,147,373 | 9/1992 | Ferizl . | |
| 5,152,744 | 10/1992 | Krause et al. | 604/22 |
| 5,174,300 | 12/1992 | Bales et al. | 128/751 |
| 5,217,479 | 6/1993 | Shuler | 606/180 |
| 5,282,821 | 2/1994 | Donahue | 606/170 |
| 5,290,308 | 3/1994 | Knight et al. | 606/205 |
| 5,330,502 | 7/1994 | Hassler et al. . | |
| 5,376,078 | 12/1994 | Dinger, III et al. | 606/170 |

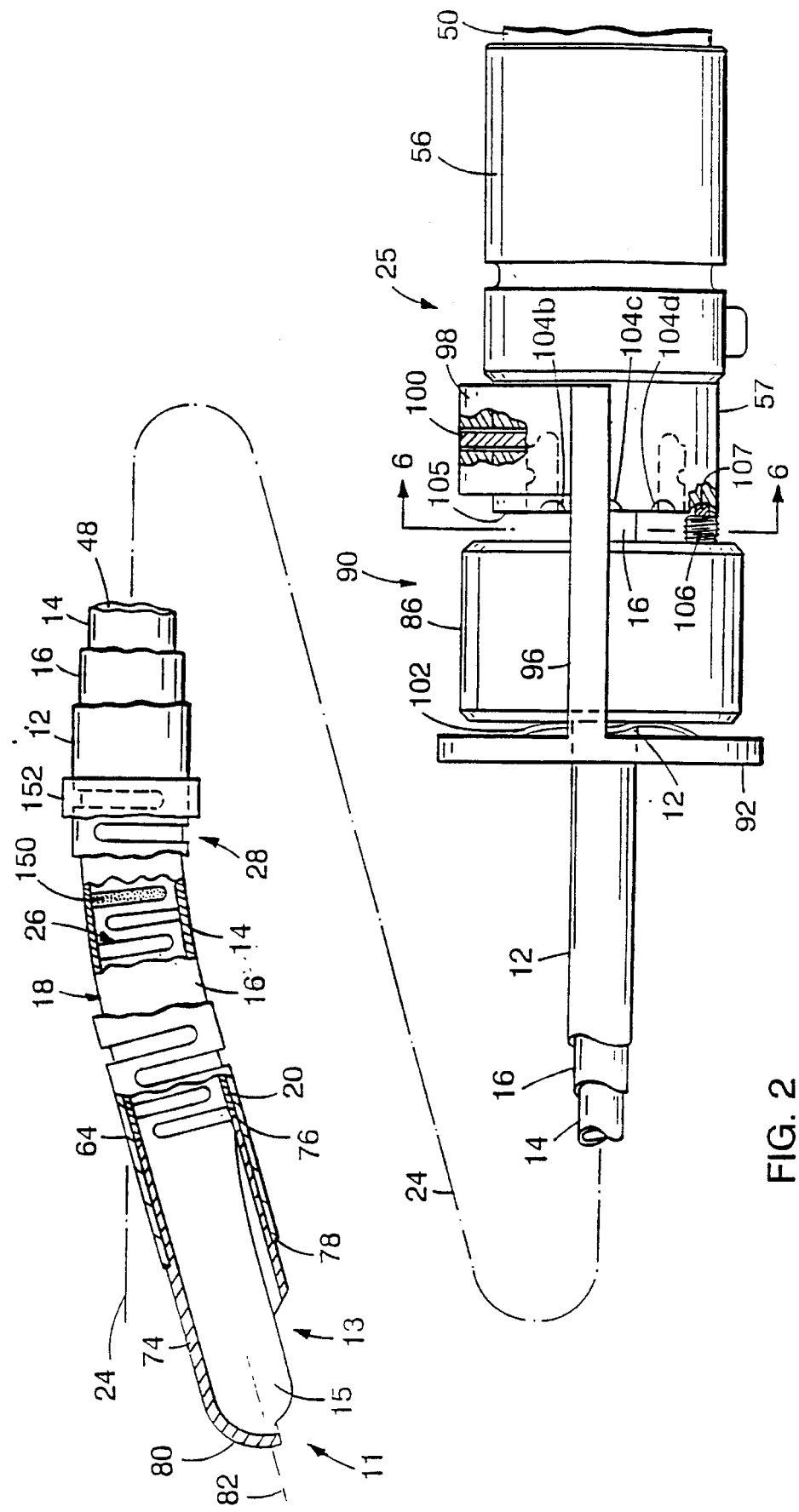

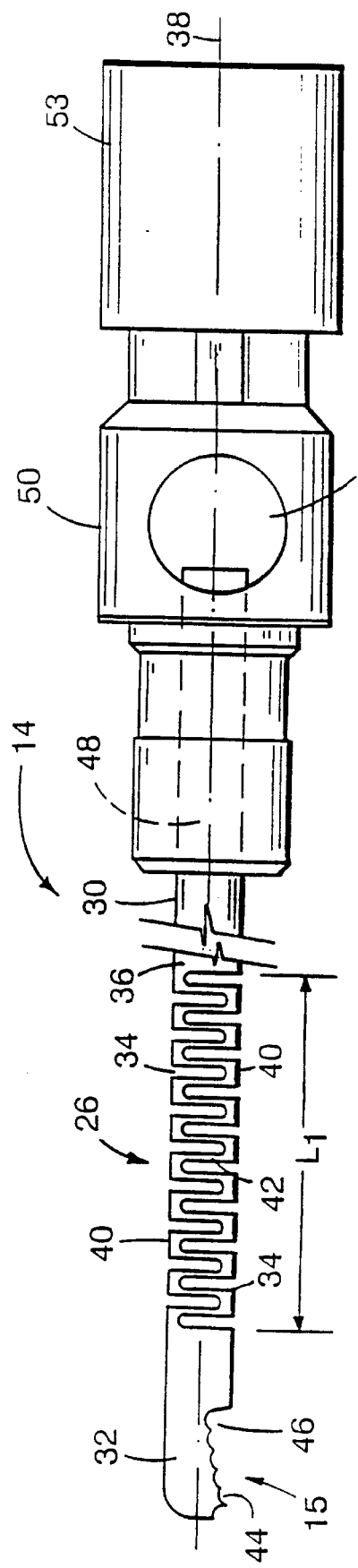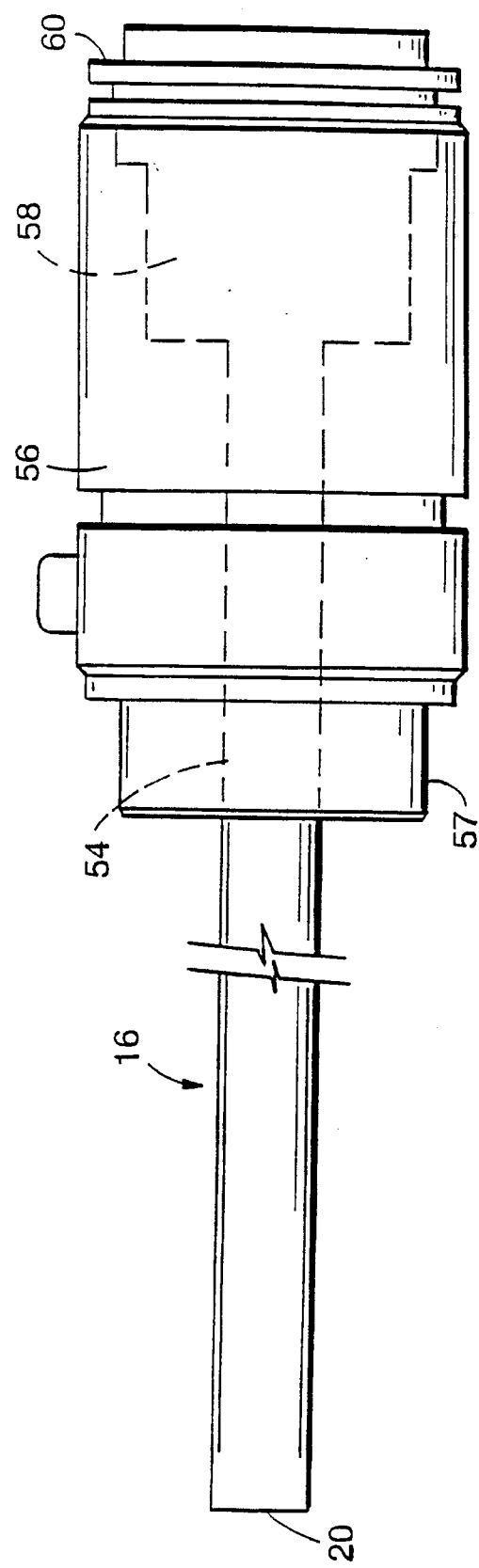

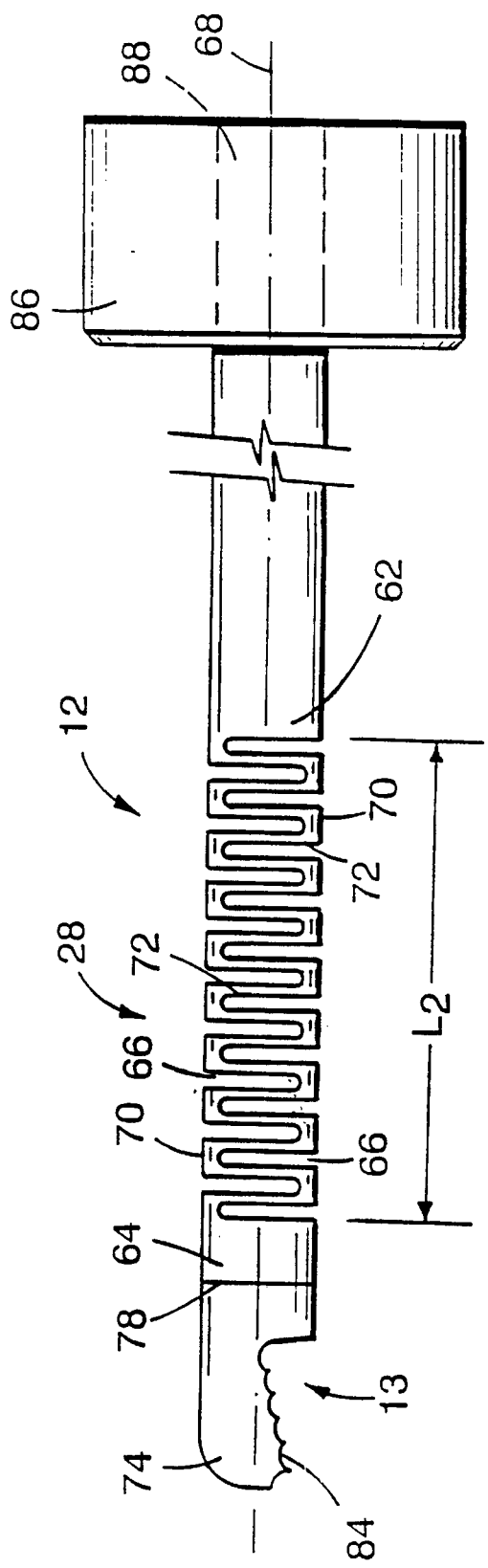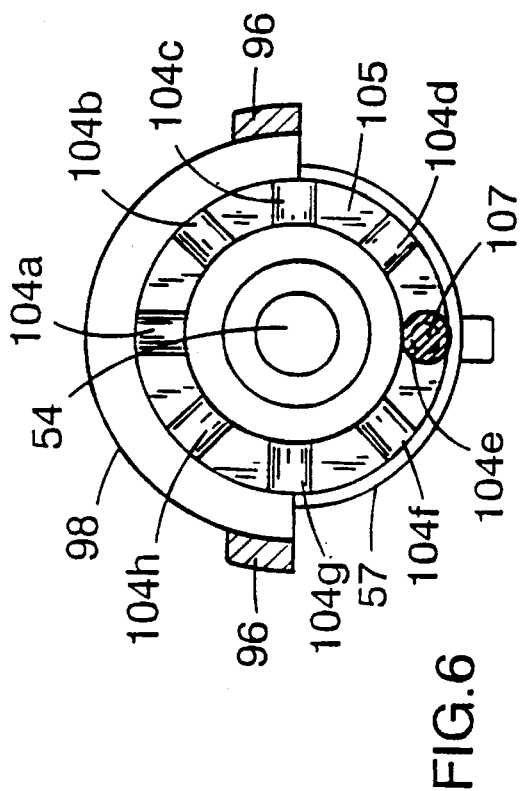
FIG. 5
FIG. 6

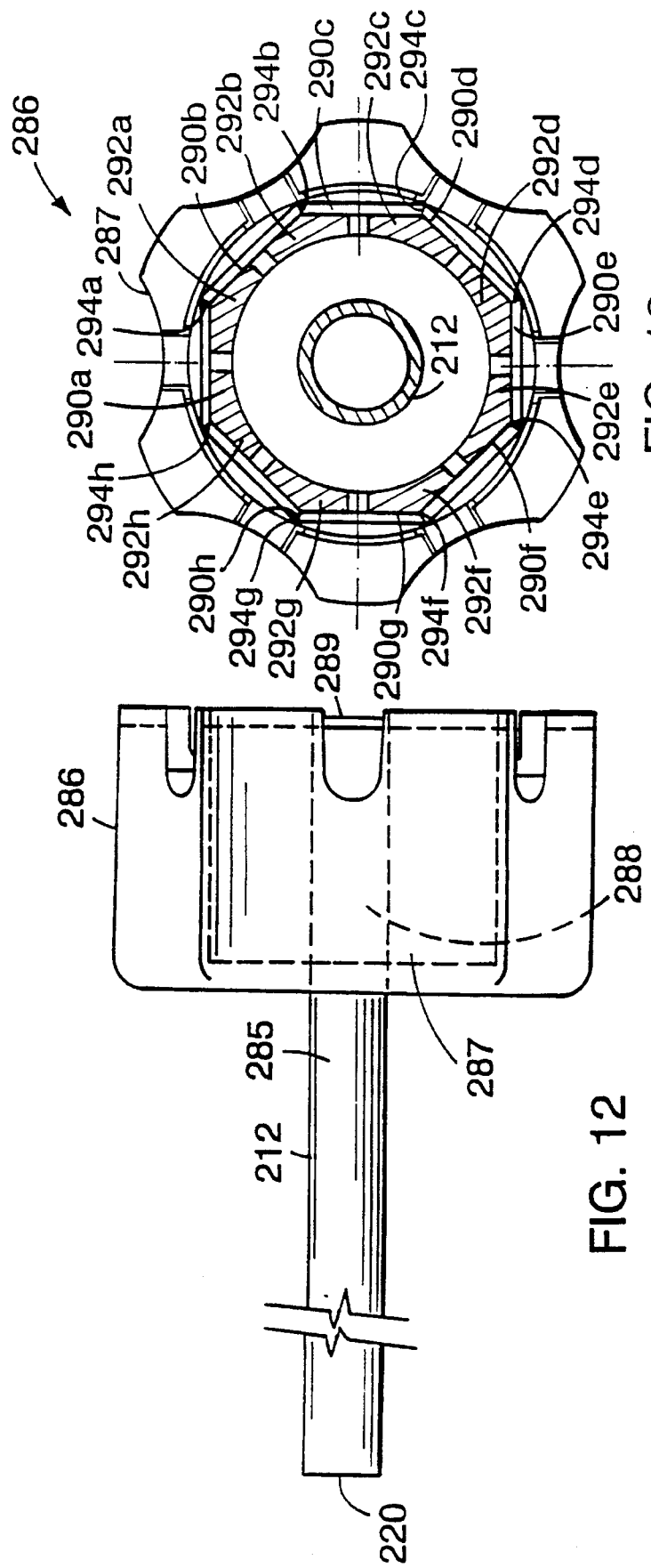

SURGICAL INSTRUMENT

CROSS REFERENCE TO RELATED APPLICATIONS

This is a continuation of application Ser. No. 08/200,662, filed Feb. 23, 1994, now abandoned, which is a continuation-in-part of application Ser. No. 08/011,364, filed Jan. 29, 1993, now abandoned, which is related to an application entitled "Surgical Instrument", filed the same day as the parent application, assigned to the present assignee, and incorporated herein by reference.

BACKGROUND OF THE INVENTION

This invention relates to surgical instruments, and in particular to powered arthroscopic surgical instruments.

Powered arthroscopic surgical instruments typically include a rigid, stationary outer tube within which a rigid inner tube is rotated by a motor. A cutting implement, such as a blade or abrading burr, is disposed on the distal end of the inner tube. Tissue or bone is exposed to the cutting implement through an opening in the distal end of the outer tube, and tissue or bone fragments cut by the rotating blade or burr are drawn through the interior of the inner tube along with irrigating fluid by the use of suction applied at the proximal end of the instrument. Examples of such surgical instruments are described in U.S. Pat. Nos. 4,203,444, 4,274,414, 4,834,729, and 4,842,578, all of which are assigned to the present assignee.

Some arthroscopic surgical instruments are linear, that is, straight between their proximal and distal ends. Others are curved to facilitate positioning the cutting implement against tissue to be cut without requiring that the instrument be removed from the body and reinserted through an additional puncture. In a curved instrument, a region of the inner tube is flexible to enable the inner tube to accept the curvature imposed by the outer tube while transmitting the torsion applied by the motor to the blade. In both cases, the user changes the orientation of the cutting implement by rotating the instrument.

SUMMARY OF THE INVENTION

A general aspect of the invention is a surgical instrument that includes a first member that has an opening in its distal region for admitting tissue and that is rotatable with respect to a base from which the first member extends to allow the rotational orientation of the opening to be selectively changed with respect to the axis of the instrument; a second member is disposed within the first member to transmit force to move a cutting implement disposed at its distal end and cause it to cut tissue that is exposed to the implement through the opening.

Among other advantages, the invention allows the user to change the angle of attack of the cutting implement (i.e, rotational orientation at which the cutting implement is exposed to tissue) by rotating the first member only, without turning the entire instrument. As a result, the user can maintain the instrument in an essentially fixed position, while rotationally varying the locations at which cutting is performed. This minimizes the manipulation required of the entire instrument, thereby facilitating the surgical procedure and reducing patient discomfort and the risk of surgical side effects.

Preferred embodiments include the following features.

In a particularly useful embodiment, the first member is provided with a bend region that angularly offsets the distal region (and hence the opening) from the axis of the instrument in a selected direction. In other words, the instrument is curved. The curved nature of the instrument allows the user (e.g., a surgeon) to position the cutting implement adjacent to tissue and other body material that is relatively difficult to reach with a straight instrument without having to remove and re-introduce the instrument through additional incisions in the body. Because the first member (rather than the entire instrument) is rotated to vary the angle of cutting attack, the cutting implement is maintained in close contact with the tissue being cut at all times.

In the curved embodiment, the first member is relatively flexible, at least in the bend region, to allow the rotational orientation of the opening to be changed without changing the direction of the offset, and at least a portion of the second member that is disposed in the bend region is also relatively flexible to transmit the applied force through the bend region to the cutting implement.

Thus, only the outer member—and not the bend region itself or the remainder of the instrument—is rotated to change the orientation of the opening. Eliminating the need to rotate the entire instrument is particularly useful with a curved instrument, because the distal region of the instrument is on an axis different from that of the remainder of the instrument. As a result, with a curved instrument in which the outer tube is nonrotatable with respect to the remainder of the instrument, the entire instrument must be pivoted or swung about the axis of the distal region of the instrument to rotate the cutting implement opening. By contrast, the present invention allows the instrument to remain in a fixed position while the opening for the cutting implement is rotated. This simplifies operation and reduces the trauma to the body.

The first member is relieved in the bend region to provide the relative flexibility. Preferably, the first member is a tube having rigid proximal and distal regions that are connected by the relieved portion. The first member is relieved with a plurality of discrete openings disposed in its walls. The openings are a series of axially spaced, circumferentially extending slots that extend radially into the first member. Adjacent slots extend into the first member from opposite directions. The configuration and orientation of the slots help ensure uniform flexibility while providing the flexible region of the first member with sufficing torsional stiffness to transmit rotation applied by the user at, e.g., the base through the bend region to rotate the opening. A pliable sheath (such as a shrink-wrap tube) may be disposed over the first member in the bend region to cover the openings.

The second member also is a tube having rigid proximal and distal ends, and the portion of the second member that lies within the bend region is relieved with a series of axially spaced, circumferentially extending slots to provide the relative flexibility. A motor applies the force as torque to the proximal end of the second member, and the slotted flexible portion is configured to transmit the torque through the bend region to rotate the cutting implement (which is, e.g., a blade). In one embodiment, pliable material is disposed in some or all of the slots. The pliable material helps avoids tissue fragments severed by the cutting implement (which, together with irrigation fluid, are removed by suction from the surgical site through the second member) from becoming lodged on the edges of the slots. The pliable material also reduces the axial compressibility of the inner tube and leaks in the suction applied to the proximal end of the inner tube.

The bend region is provided by a rigid member that is disposed coaxially with the first and second members and is curved in the bend region. The rigid member radially separates the first member from the second member at least in the bend region. This helps avoid interference between the flexible regions (e.g., the edges of the slots) as the second member moves. Preferably, the second member is disposed within the rigid member, which is in turn disposed within the first member.

The rigid member has an open distal tip disposed proximally of the cutting implement and opening, and the first and second members are configured to contact each other distally of the tip to maintain the cutting implement in tissue cutting relationship with edges of the opening. A portion of the distal region of the first member has a reduced inner diameter with respect to the remainder of the first member to provide the contact with the second member and abuts the tip of the rigid member. The reduced inner diameter equals the inner diameter of the rigid member to provide a substantially smooth chamber within which the second member rotates, thus reducing the risk of the inner member seizing as it rotates.

The first member is rotatable to allow orientation of the opening to be changed over an arc of at least 180°, and preferably over a range of 360°. The outer tube is rotated manually, using a knob that is rigidly secured to a proximal end of the first member and rotatably mounted to a stationary portion of the base. A ratchet mechanism mounts the knob to the base to allow the knob to be selectively rotated to a plurality of discrete positions, thereby to allow the opening for the cutting implement to be selectively positioned to a corresponding plurality of discrete rotational orientations.

The stationary portion includes a plurality of recesses each of which corresponds to one of the discrete positions, and the knob has a plunger that selectively engages the recesses to maintain the opening in the discrete rotational orientation that the user has selected. The knob is resiliently biased toward said stationary portion to retain said plunger in a recess. This helps avoid accidental rotation of the first member with respect to the base.

The proximal end of the second member is secured to a drive shaft mounted for movement (e.g., rotation) with respect to the stationary portion and the knob. The drive shaft is driven by a motor to rotate the second member with respect to the first member and move the cutting implement. The second member receives suction at its proximal end to draw tissue fragments and other body material cut by the cutting implement through the second member away from a surgical site while the instrument remains in situ for further cutting.

In another aspect of the present invention, a surgical instrument includes a rigid member that has a bend region that angularly offsets a distal region from a proximal region mounted to a first section of a base; a surgical device extending distally from a second section of the base coaxially with the rigid member carries a surgical tool distal of the bend region, and is flexible at least in the bend region to transmit force applied at a proximal end of the surgical device through the bend region to operate the surgical tool; the first base section is rotatable with respect to the second base section, allowing the relative rotational orientation between the surgical tool and the bend region to be changed.

Among other advantages, this feature of the invention allows the user to change the relative rotational orientation between the surgical tool and the bend region. Accordingly, without turning the instrument and without changing the direction of offset of the bend region, the user can rotationally vary the direction in which cutting is performed. Alternatively, the user can, without turning the instrument and without changing the direction in which cutting is performed, change the direction of offset of the bend region. Thus, with only minimal manipulation of the instrument, the surgical tool can be positioned to cut tissue at a variety of locations in a given surgical site.

Eliminating the need to turn the entire instrument is particularly useful with a curved instrument, because the distal region of the instrument is on an axis different from that of the remainder of the instrument. As a result, if the relative rotational orientation between the surgical tool and the bend region could not be changed, the entire instrument would have to be pivoted or otherwise swung about the axis of the distal region of the instrument to rotate the surgical tool. Because it allows the instrument to remain in a fixed position while the rotational orientation of the surgical tool is changed with respect to the bend region, the present invention thereby facilitates the surgical procedure and reduces patient trauma and the risk of surgical side effects.

Preferred embodiments include the following features.

The surgical device includes a second member coaxially disposed within a first member, such that the first member mounts to the second section of the base, and the second member moves with respect to the first member in response to the force applied at the proximal end of the surgical device. The first member is coaxially disposed within the rigid member; or, alternatively, the rigid member is coaxially disposed within the first member, and the second member is coaxially disposed within the rigid member. Preferably, the first member is hollow and adapted to receive suction at its proximal end, allowing body material cut by the surgical tool to be transported away from the surgical site while the instrument remains in situ.

Both the first member and the second member are relieved (e.g., with a series of axially spaced, circumferentially extending slots) in the relatively flexible region. Pliable sheaths (such as heat-shrink tubing) are disposed over the first and second members to cover the slots. The pliable sheaths reduce the axial compressibility of the first and second members, minimize vacuum, tissue, fluid, and other leakage between the first, second, and rigid members, and protect the flexible regions from excessive wear as the first and second members rotate. The pliable sheath disposed over the slots of the second member further prevents the slots of the second member from interfering with the slots of the first member.

The surgical tool is preferably comprised of openings at the distal regions of the first and second members, the openings being arranged such that an edge of the opening in the first member moves toward and closely past an edge of the opening in the second member to cut tissue entering through the openings when force (e.g., torque) is applied (e.g., by a motor) to the first member.

The first section of the base is rotatable (e.g., manually by the user) with respect to the second section to allow the relative rotational orientation between the surgical tool and the bend region to be changed over a range of at least 360°. A ratchet mechanism allows the first section of the base to be selectively rotated to a plurality of discrete positions with respect to the second section, thereby also allow the relative rotational orientation between the surgical tool and the bend region to be selectively changed to a corresponding plurality of discrete relative rotational orientations.

Preferably, to provide this ratchet mechanism the second section includes a plurality of flexible cantilevered fingers, each of which corresponds to a discrete position, and the first section includes a plurality of mating regions, each of which engages one finger. This mechanism thereby avoids accidental rotation of the surgical tool with respect to the bend region.

Other features and advantages of the invention will become apparent from the following detailed description, and from the claims.

BRIEF DESCRIPTION OF THE DRAWINGS

FIG. 2 is a partial cross-sectional view of portions of the instrument of FIG. 1, showing details of the tip and base.

FIGS. 3–5 show inner, intermediate, and outer tubes, respectively, of the surgical instrument of FIG. 1.

FIG. 6 is a cross-section of the base of the surgical instrument, taken along line 6—6 of FIG. 2.

FIGS. 10–12 show inner, intermediate, and outer tubes, respectively, of the surgical instrument of FIG. 8.

FIG. 13 is a cross-section of the surgical instrument, taken along line 6—6 of FIG. 9.

DESCRIPTION OF THE PREFERRED EMBODIMENT

Figure 1:
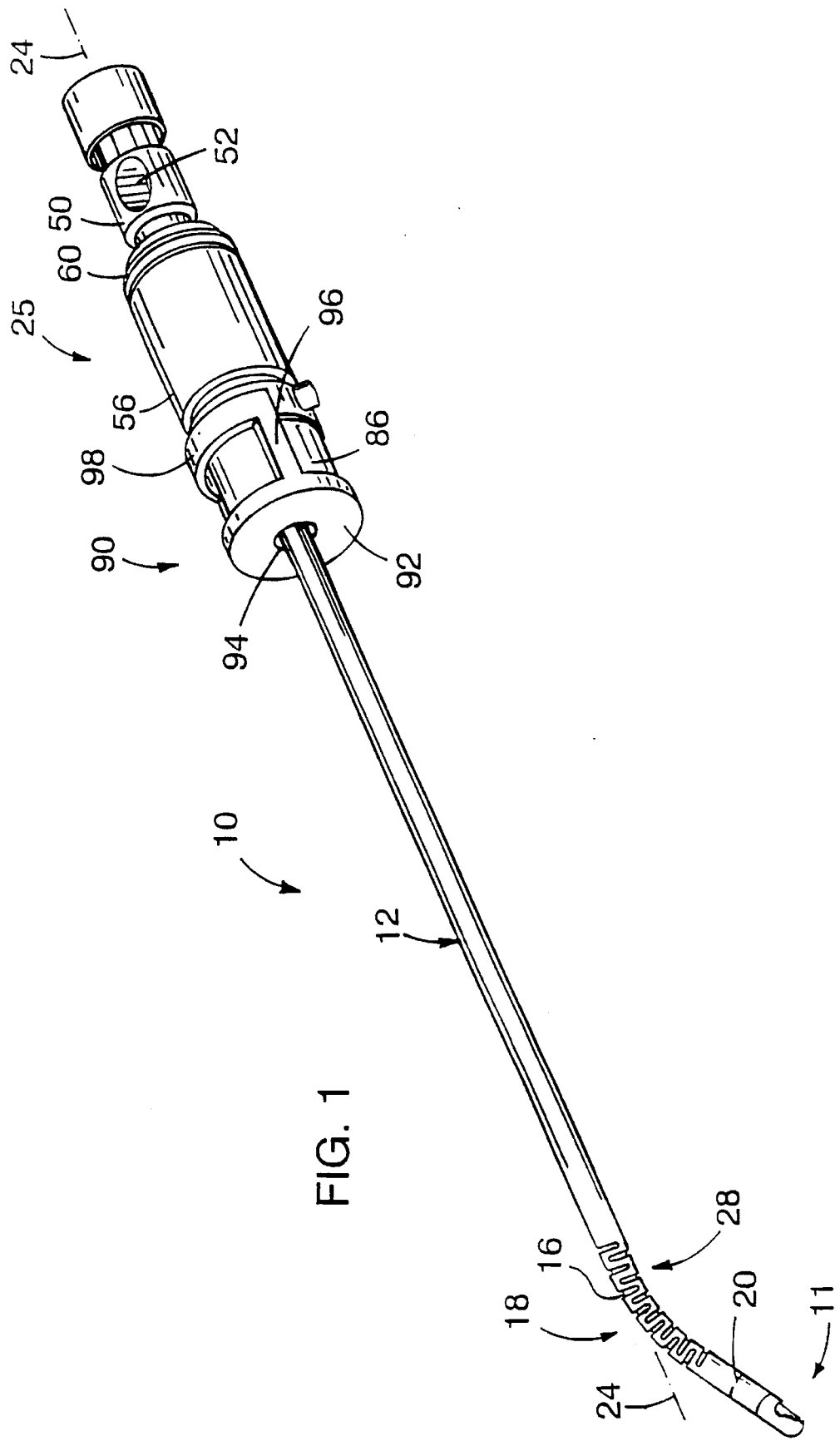
FIG. 1 shows a surgical instrument according to the invention, having a cutting implement that is adjustable to different rotational positions.

Referring to FIGS. 1 and 2, surgical instrument 10 suitable for performing, e.g., closed, arthroscopic surgery on the knee with a surgical tool 11, includes an outer tube 12 within which a rotating inner tube 14 is coaxially disposed. The distal end of outer tube 12 includes an opening 13, the edges of which are sharpened and serrated, through which a cutting implement 15 (formed by sharpened, serrated edges of a similar opening in the distal end of inner tube 14) of surgical tool 11 is periodically exposed as inner tube 14 rotates. A rigid, stationary intermediate tube 16 is disposed coaxially between outer tube 12 and inner tube 14. Intermediate tube 16 is curved through a bend region 18 disposed slightly proximally of the distal end 20 of tube 16 to angularly offset surgical tool 11 from a generally straight axis 24 of surgical instrument 10. Bend region 18 enables surgical instrument 10 to operate on surgical areas that are difficult to reach with a straight instrument.

Tubes 12, 14, and 16 are proximally supported by a base 25. As discussed in detail below, inner tube 14 includes a slotted, flexible region 26 disposed within bend region 18 to accept the curvature imposed by bend region 18 and transmit torque (and other forces) applied at base 25 through bend region 18 to rotate cutting implement 15 with sufficient force to sever tissue or other body material exposed through opening 13. Outer tube 12 has a slotted, flexible region 28 that envelopes bend region 18 and allows the user to rotate outer tube 12 with respect to base 25, despite the curvature imposed by bend region 18. This feature enables the user to selectively change the rotational orientation of opening 13—and hence surgical tool 11—with respect to axis 24 without rotating the entire surgical instrument 10, and thus without changing the orientation of bend region 18 and the angular offset that it provides. As a result, the user can maintain surgical instrument 10 in an essentially fixed position, while changing the angle of attack of cutting implement 15 by rotating outer tube 12.

Referring also to FIG. 3, inner tube 14 is made from metal, such as stainless steel, and has rigid proximal and distal regions 30, 32, that are connected by flexible region 26. Flexible region 26 is relieved with an axially extending series of circumferential slots 34 disposed in the walls 36 of tube 14 and is continuous with the adjacently disposed proximal and distal regions 30, 32. (Slotting a rotatable tube for flexibility is described in a copending application entitled "Surgical Instrument," Ser. No. 07/634,599, now U.S. Pat. No. 5,152,744, filed on Dec. 27, 1990, assigned to the present assignee and incorporated herein by reference.) Slots 34 are perpendicular to the longitudinal axis 38 of tube 14 and are arranged in a symmetrical pattern along the length $L_1$ of flexible region 26 to provide uniform flexibility and avoid any substantial deviation in flexibility as inner tube 14 rotates. This minimizes torsional stresses on inner tube 14 and helps prolong the operating life of surgical instrument 10.

Slots 34 are disposed parallel to each other (vertically in FIG. 3) along length $L_1$. Adjacent slots 34 extend into tube 14 from opposite directions (e.g., from above and below tube 14 in FIG. 3) and are circumferentially offset from each other by 180°. The number of slots 34, their dimensions (i.e., their width and depth), and the spacing between adjacent slots are a function of the desired degree of flexibility. For example, the width of each slot 34 and the spacing between slots 34 each are 0.020 inches (0.508 mm).

A tab 40 bounds each slot 34 circumferentially, and adjacent tabs 40 are interconnected by annular rings 42, which provide the spacing between adjacent slots 34. The interconnected series of rings 42 and tabs 40 provide a series of interconnected, integrally formed "U" shaped leaf springs along the length $L_1$ of flexible region that give uniform flexibility and efficiently transmit torque (i.e., rotational force) applied at proximal region 30 of tube 14 to distal region 32 through the curvature imposed by bend region 18 (FIG. 1). The depth of slots 34 (i.e., the amount by which slots 34 extend radially into tube 14) is a function of the desired torsional strength of flexible region 26. For example, slots 34 have a depth of about 75% of the outer diameter (0.135 inches, or 3.429 mm) of inner tube 14.

The length $L_1$ of flexible region 26 is a function of the length of bend region 18. Flexible region 26 should be sufficiently long (e.g. 0.70 inches, or 17.78 mm) so as to span the entire length of bend region 18, with adjacent rigid regions 30, 32 lying within straight regions of stationary intermediate tube 16. This allows flexible region 26 to make a smooth transition between the straight regions of intermediate tube 16 and bend region 18, thereby reducing stresses imposed by the curved inner walls of bend region on walls 36 of inner tube 14.

Flexible region 26 can be formed by any suitable method. Examples include wire EDM (electric discharge machining) and sawing. Both are described in the aforementioned U.S. patent application Ser. No. 07/634,599, now U.S. Pat. No. 5,152,744.

Distal region 32 of inner tube 14 supports cutting implement 15 (which is, for example, stainless steel and attached to tube 14 by welding or brazing). Cutting implement 15 is defined by serrated, sharpened edges 44 of a distal opening 46 in tube 14 and is sized to provide a close running fit with the distal end of outer tube 12 for efficient cutting. Opening 46 is an extension of a central aperture 48 in inner tube that runs the entire length of tube 14.

Proximal region 30 of inner tube 14 is rigidly mounted to a drive shaft 50 that rotates within base 25. Central aperture 48 terminates in a vacuum source opening 52 in drive shaft 50. The proximal end 53 of drive shaft 50 fits into a handpiece 110 (FIG. 7), which includes a motor 112 for rotating drive shaft 50 and inner tube 14 with respect to tubes 12, 16. One example of such a handpiece is described in U.S. Pat. No. 4,705,038, entitled "Surgical System for Powered Instruments", and assigned to the present assignee, which is incorporated by reference. Opening 52 is coupled to a vacuum source 114 (FIG. 7) during operation to remove severed tissue and irrigating fluid from the surgical site via aperture 48 in a manner described in detail below.

FIG. 4 shows intermediate tube 16 (before bend region 18 is formed), which is made from a rigid material such as metal (e.g., stainless steel). Intermediate tube 16 is hollow along its entire length to provide a passage 54 that receives inner tube 14, which protrudes through the open distal end 20 of intermediate tube 16 (FIG. 2). The inner diameter of intermediate tube 16 is only slightly larger than the outer diameter of inner tube 14 (e.g., by approximately 0.002 inches, or 0.051 mm); this allows inner tube 14 to rotate freely but helps minimize wobbling of tube 14 to keep the sharp cutting edges of implement 15 and opening 13 closely aligned.

The proximal end of intermediate tube 16 is rigidly mounted to a hub 56 of base 25. A cavity 58 in hub 56 communicates with passage 54 and is configured to receive drive shaft 50. During assembly, inner tube 14 is inserted through hub 56 into intermediate tube 16 (before bend region 18 is formed). A pliable fitting 60 retains drive shaft 50 within hub 56. Fitting 60 provides a fluid-tight seal when base 25 is inserted into handpiece 110.

Referring to FIG. 5, outer tube 12 is essentially a larger version of inner tube 14 and includes rigid proximal and distal regions 62, 64 that are integrally connected by flexible region 28. Flexible region 28 includes an axially extending series of slots 66 disposed perpendicularly to the longitudinal axis 68 of tube 12 and arranged in a symmetrical pattern along the length $L_2$ of flexible region 28. Adjacent slots 66 extend radially into tube 12 in opposite directions (i.e., from above and below tube 12 in FIG. 5). Each slot 66 is approximately 0.025 inches (0.635 mm) wide and has a depth of about 0.140 inches (3.556 mm).

Each slot 66 is bounded by a tab 70. Adjacent tabs 70 are circumferentially offset by 180° and are connected by rings 72 (each of which has the same width as slots 66) to form a series of "U" shaped springs that are continuous with each other and with proximal and distal regions 62, 64. As a result, flexible region 28 is both sufficiently pliable to accept the curvature imposed by bend region 18 and sufficiently torsionally stiff to transmit applied rotational force through bend region 18 to rotate opening 13. Length $L_2$ should be such that flexible region 28 spans the entire length of bend region 18, with the adjacently-disposed rigid portions 62, 64 of outer tube being aligned with straight portions of intermediate tube 16.

As shown most clearly in FIG. 2, to ensure a close running fit between sharp edges 44 of cutting implement 15 and the corresponding cutting edges 84 of opening 13 despite the spacing between tubes 12, 14 that intermediate tube 16 provides, a distal extension 74 having the same inner diameter as intermediate tube 16 is secured to outer tube 12 at distal end 64. Extension 74 is, e.g., stainless steel, and is welded or brazed to outer tube 12, which can be a softer material, such as aluminum. The proximal end of extension 74 has a reduced outer diameter to allow it to be disposed within outer tube 12 and abut intermediate tube 16 at joint 76. A shoulder 78 on distal extension 74 limits the amount by which extension 74 is inserted into distal end 64 during assembly.

Opening 13 is disposed in a distal tip 80 of extension 74 and faces somewhat to the side of outer tube 12. That is, opening 13 does not extend completely to the centerline 82 of extension 74. As a result, while surgical tool will cut tissue that enters opening 13 from the distal end of instrument 10, the majority of the cutting action is to one side. Moreover, tip 80 provides distal support for the rotating inner tube 14. The edges 84 of opening 13 are sharpened and serrated to cooperate with sharp edges 44 of cutting implement 15. The clearance between inner tube 14 and the inner diameter of outer tube extension 74 and intermediate tube 16 is small (e.g., approximately 0.002 inches, or 0.051 mm) to maintain the close running fit between edges 44, 84 while allowing inner tube 14 to rotate freely. The identical inner diameters of extension 74 and intermediate tube 16 avoid inner tube 14 scoring or seizing as it rotates.

Proximal region 62 (FIG. 5) of outer tube 12 is rigidly secured to a drum 86 at a sealed joint. Drum 86 serves as a knob to enable the user to manually rotate tube 14, and is rotatably mounted to base 25 in a manner described below. A central passage 88 extends through outer tube 12 and drum 86 to receive intermediate tube 16 and inner tube 14. The inner diameter of outer tube 12 (proximally of extension 74) only slightly exceeds the outer diameter of intermediate tube 16 (e.g., by approximately 0.002 inches, 0.051 mm). This allows the user to rotate outer tube 12 but avoids excessive play between tubes 12, 16.

Referring to FIG. 2, outer tube 12 and drum 86 are rotatably mounted to base 25 with a spring-loaded rotation assembly 90. Drum 86 is captured between the distal end 57 of hub 56 and a faceplate 92, which includes an opening 94 (FIG. 1) through which outer tube 12 projects. A pair of axially extending bars 96 connect faceplate 92 to a sleeve 98 that is rigidly mounted to hub distal end 57 by one or more press-fit pins 100. A spring 102 (e.g., a wave washer), which fits within a recess (not shown) in faceplate 92, resiliently biases drum 86 toward hub 56.

Referring also to FIG. 6 (which, for clarity does not show tubes 14, 16 in cross-section), distal end 57 of hub 56 includes a series of (such as eight) rounded recesses 104a–104h disposed in an annular surface 105 of hub 56 that faces drum 86. Recesses 104a–104h are spaced by equal amounts (such as by 45°) around the circumference of hub 56. Surface 105 is flat between adjacent recesses 104a–104h. A plunger 106 having a spring-loaded, ball shaped tip 107 is threaded into drum 86. Tip 107 is resiliently urged against hub 56 and into a selected one of recesses 104a–104h by spring 102.

Thus, the user can selectively rotate drum 86—and hence outer tube 12 and surgical tool opening 13—to one of eight discrete rotational orientations. The biasing provided by spring 102 maintains plunger tip 107 in the selected recess 104a–104h to avoid accidental rotation. As drum 86 is rotated between recesses 104a–104h, tip 107 is compressed into plunger 106 by flat surfaces 105. Recesses 104a–104h are arranged to allow opening 13 to be rotated in a ratchet-like fashion to commonly used positions with respect to axis 24. For example, positioning plunger tip 107 in recess 104a orients opening 13 oppositely from the direction of curvature of bend region 18 (FIG. 2), that is, upwardly. With plunger 106 moved to recess 104e, opening 13 is aligned with the curvature direction and is oriented downwardly (the position shown in FIG. 2). Similarly, recesses 104c and 104g correspond to left and right orientations. Recesses 104b, 104d, 104f, and 104h provide intermediate positions for opening 13.

Figure 7:
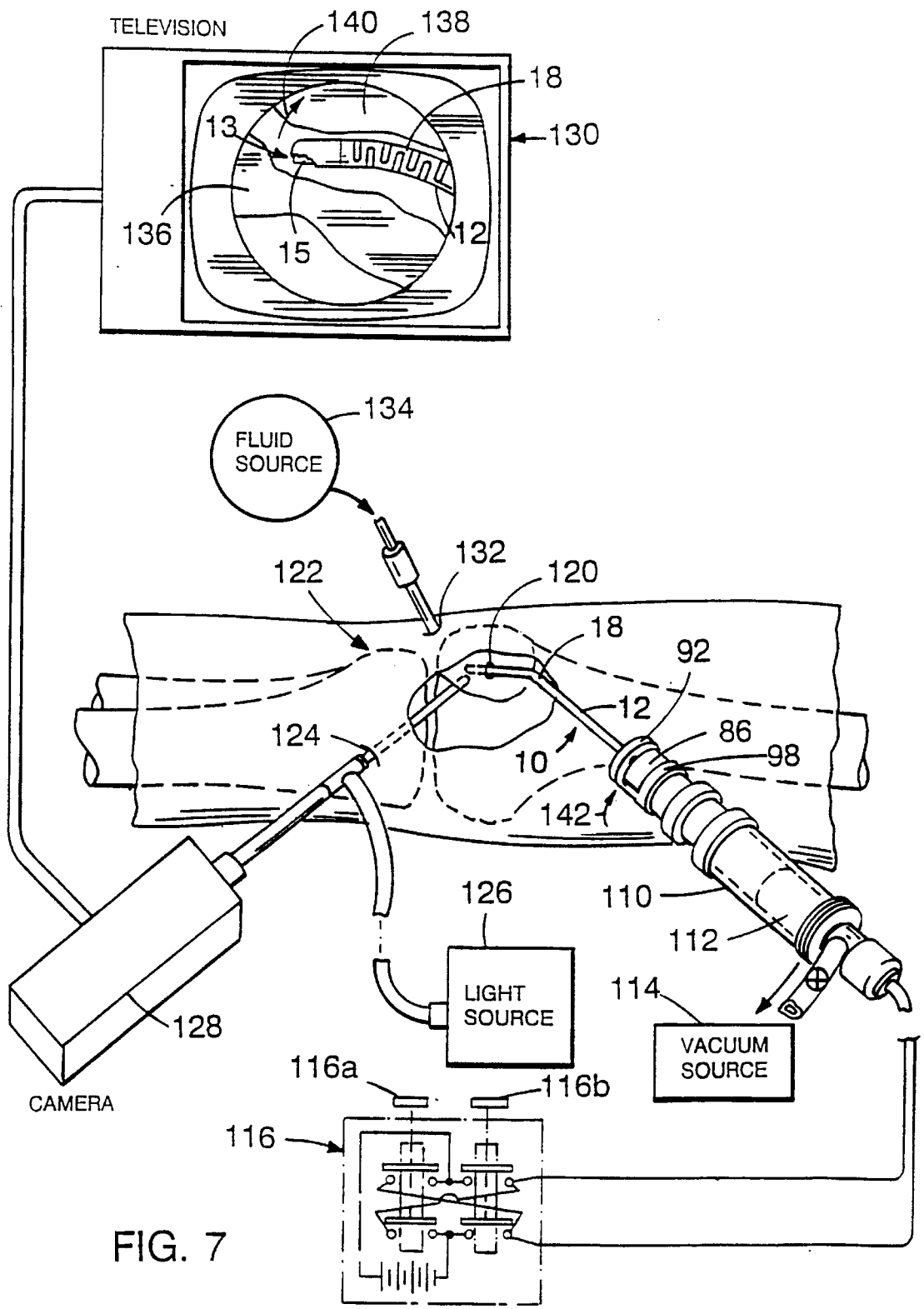
FIG. 7 shows the surgical instrument of FIG. 1 in use.

Referring also to FIG. 7, in operation, surgical instrument 10 is inserted into the distal end of a handpiece 110 and is introduced as shown through a puncture wound 120 into the knee joint 122, below the patella. Light is projected into the joint via a second puncture 124 using a fiber optic light source 126, and a visual image of the surgical site is returned through a separate optical path to a television camera 128. The image is delivered by camera 128 onto a television screen 130 for viewing by the surgeon. (Alternatively, the surgeon can view the image using an eyepiece, or the image can be recorded.)

The surgeon operates surgical tool 11 by activating motor 112, which receives operating potential and current from power supply 116. Motor 112 engages and rotates drive shaft 50, thereby applying rotational force to inner tube 14 and rotating tube 14 with respect to tubes 12, 16. The surgeon controls rotational speed and direction (either unidirectional or oscillatory) using foot switches 116a, 116b, which control the magnitude and polarity of operating potential and current provided by power supply 116 to motor 112. Motor 112 is capable of rotating inner tube 14 over a wide range of speeds, e.g., between about 100 rpm and 5000 rpm, and can deliver a torque of up to 25 oz. inches (0.177 Nm).

Different types of surgical instruments such as instrument 10 have rotational and torsional limits. To prevent the surgeon from inadvertently operating instrument 10 at dangerously high speeds and torques, instrument 10 identifies to sensors (not shown) in handpiece 110 what type of instrument it is, and the speed of and torsion applied by motor 112 is controlled so that these limits are not exceeded. (This control technique is described in the aforementioned U.S. Pat. No. 4,705,038.)

The torsion that motor 112 provides is efficiently delivered to cutting implement 15 by flexible region 26. Although region 26 is sufficiently flexible to accept the curvature imposed by bend region 18, it has a high degree of torsional stiffness and thus provides good torque response. That is, torsion applied by motor 112 is transmitted to distal region 32 of inner tube 14 substantially immediately when inner tube 14 is rotated from its rest position, without requiring any significant "preloading" of flexible region 26 prior to passing the torque to distal end 32. Also, flexible region 26 does not expand in diameter by any significant amount as it rotates and applies torque to distal end 32, reducing the possibility that tube 14 will bind within intermediate tube 16 during rotation.

During the surgical procedure, the body joint is distended with fluid introduced through a third puncture wound 132 from a fluid source 134. The fluid irrigates the site and renders tissue 136 (which is, e.g., synovial tissue) mobile so that it floats and can be displaced (similar to the movement of seaweed in water). Note that synovial tissue 136 is located beneath outer tube 12; thus, drum 86 is positioned so that plunger 106 is in recess 104e (FIGS. 2 and 6). The curvature provided by bend region 18 allows surgical instrument 10 to be easily positioned to place surgical tool 11 against tissue 136 (even if tissue 136 is located in a region of the joint that cannot easily be reached by a straight instrument) without manipulating instrument 10 unduly or requiring that additional punctures be made to gain access to tissue 136. This reduces patient discomfort, as well as the chances for infection and other deleterious consequences of the surgery.

The surgeon progressively cuts away synovial tissue 136 by moving surgical instrument 10 from side to side and in the axial direction using handpiece 110 (while viewing television screen 130). If during the procedure the surgeon wishes to cut tissue from another region of the synovial tissue, such as region 138 located above outer tube 14, the present invention allows him to do so simply by changing the rotational orientation of surgical tool opening 13 (e.g., in the direction of arrow 140) while maintaining handpiece 110 in a fixed position—that is, without requiring the surgeon to rotate or pivot handpiece 110.

This is accomplished, for example, by grasping drum 86 with the finger and thumb of one hand (while the other hand continues to grasp the body of handpiece 110) and turning drum 86 in the direction in which opening 13 is selected to rotate (e.g., along arrow 142). The rotational force applied by the surgeon is transmitted through bend region 18 by flexible region 28, thereby causing distal extension 74 of outer tube 12 to rotate with respect to intermediate tube 16 and base 25 and change the orientation of opening 13 with respect to axis 24 (in this case, by 180°).

In this example, in which tissue 138 is located above outer tube 12, the surgeon continues to rotate drum 86 until plunger 106 rests within recess 104a. As drum 86 is rotated between recesses, plunger 106 slides across flat surface 105 and drum 86 compresses spring 102 against faceplate 94. Thus, spring 102 positively urges plunger 106 into each recess 104 as it is encountered, thereby giving the surgeon kinesthetic feedback as to the amount by which opening 13 has been rotated.

The surgeon can change the rotational orientation of opening 13 at any time. For example, inner tube 14 can be driven by motor 112 or may be stationary while the surgeon rotates opening 13. Distal extension 74 rotates smoothly with respect to the stationary intermediate tube 16 at joint 76, while providing constant distal support (at tip 80) for rotating inner tube 14. The identical inner diameters of tube 16 and extension 74 help ensure that the rotation of outer tube 12 does not cause inner tube 14 to bind or seize. The surgeon can return to cutting tissue 136 at any time simply by rotating drum 86, either in the opposite direction from arrow 142 or in the same direction to trace a 360° arc from his starting point.

Tissue fragments and other body material cut by surgical tool 11 are withdrawn from the surgical site along with irrigation fluid via central aperture 48 of inner tube 14 (FIG. 2) in response to suction applied by vacuum source 114. Note that as flexible region 26 rotates within the bend region 18, the width of each slot 34 at the periphery of tube wall 36 progressively increases and decreases incrementally with respect to its nominal width. This is because flexible region 26 tends to stretch at the apex of bend region 18 (i.e., the upper part of bend region 18 in FIG. 2) and compress at the base of the bend. This alternating widening and constricting as tube 14 rotates may generate turbulence in the fluid being withdrawn through aperture 48, thereby assisting in the transport of tissue fragments through the chamber and out of surgical instrument 10.

The exposure of aperture 48 to the interior walls of intermediate tube 16 through slots 34 has not been found to allow tissue fragments to become caught in the slots and cause blockage, perhaps due to the small width of the slots and the continual rotation of inner tube 14. Fluid likewise has not been found to seep between tubes 14, 16 via slots 34 (or between tubes 12, 16) in amounts that interfere with the operation of instrument 10.

Other embodiments are within the scope of the following claims.

For example, although surgical instrument 10 is shown with bend region 18 oriented downwardly with respect to axis 24 and handpiece 25, it is readily apparent that other orientations (e.g., downwardly, to the right or left, or anywhere in between these directions) are possible. Indeed, a set of surgical instruments may be provided, each with a different bend region 18 orientation, to give the user maximum flexibility in determining the optimum bend configuration for a given surgical procedure other amounts of curvature can be provided.

Also, as described in the aforementioned patent application Ser. No. 07/634,599, now U.S. Pat. No. 5,152,744, pliable material (such as silicone rubber) may be disposed in slots 34 of inner tube 14. (Pliable material is illustrated in FIG. 2 by shaded area 150 within a slot 34 of inner tube 14.) The pliable material would further help avoid clogging by reducing the tendency of tissue fragments to become caught on the edges of slots 34 as the fragments pass through inner tube 14. Moreover, the pliable material is less compressible than empty space, and thus would serve to reduce the axial compressibility of flexible region 26.

A tube (made from, e.g., shrink wrap plastic) may be placed over outer tube in bend region 18 to cover slots 66. (A portion of such a tube 152 in shown in FIG. 2.) Among other advantages, a shrink wrap tube will avoid material becoming lodged within slots 66 and help prevent the edges of slots 66 (which may be sharp) from causing damage.

Surgical tools other than the cutting implement shown in the figures can be used. For example, the surgical tool need not have serrated edges and may alternatively be constructed as a bone abrading instrument. The surgical instrument can be constructed to perform procedures other than arthroscopy (such as laparoscopy).

Inner tube 14 may alternatively be flexible along its entire length so long as the tube is sufficiently stiff to transmit the forces applied to it (e.g., torsion) to surgical tool 11. For example, inner tubes 14 may comprise a nonmetal, such as plastic, and drive a separate, metal member that carries cutting implement 15. Such a configuration is shown in copending application Ser. No. 07/978,178, filed on Nov. 17, 1992, which is a continuation of application Ser. No. 07/600,531, filed on Oct. 19, 1990, which are both assigned to the present assignee and incorporated herein by reference.)

Figure 8:
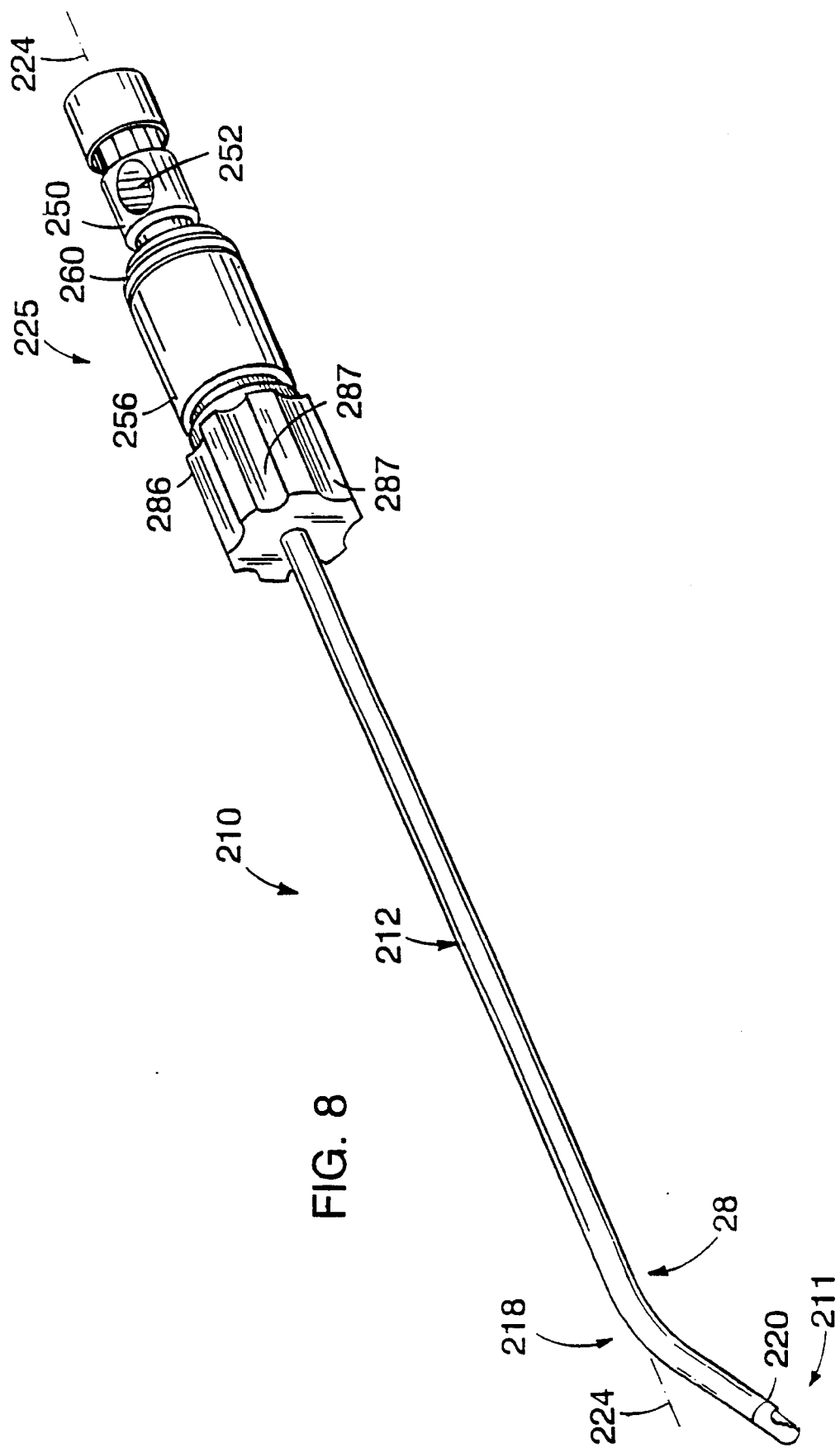
FIG. 8 shows another embodiment of a surgical instrument according to the invention.
Figure 9:
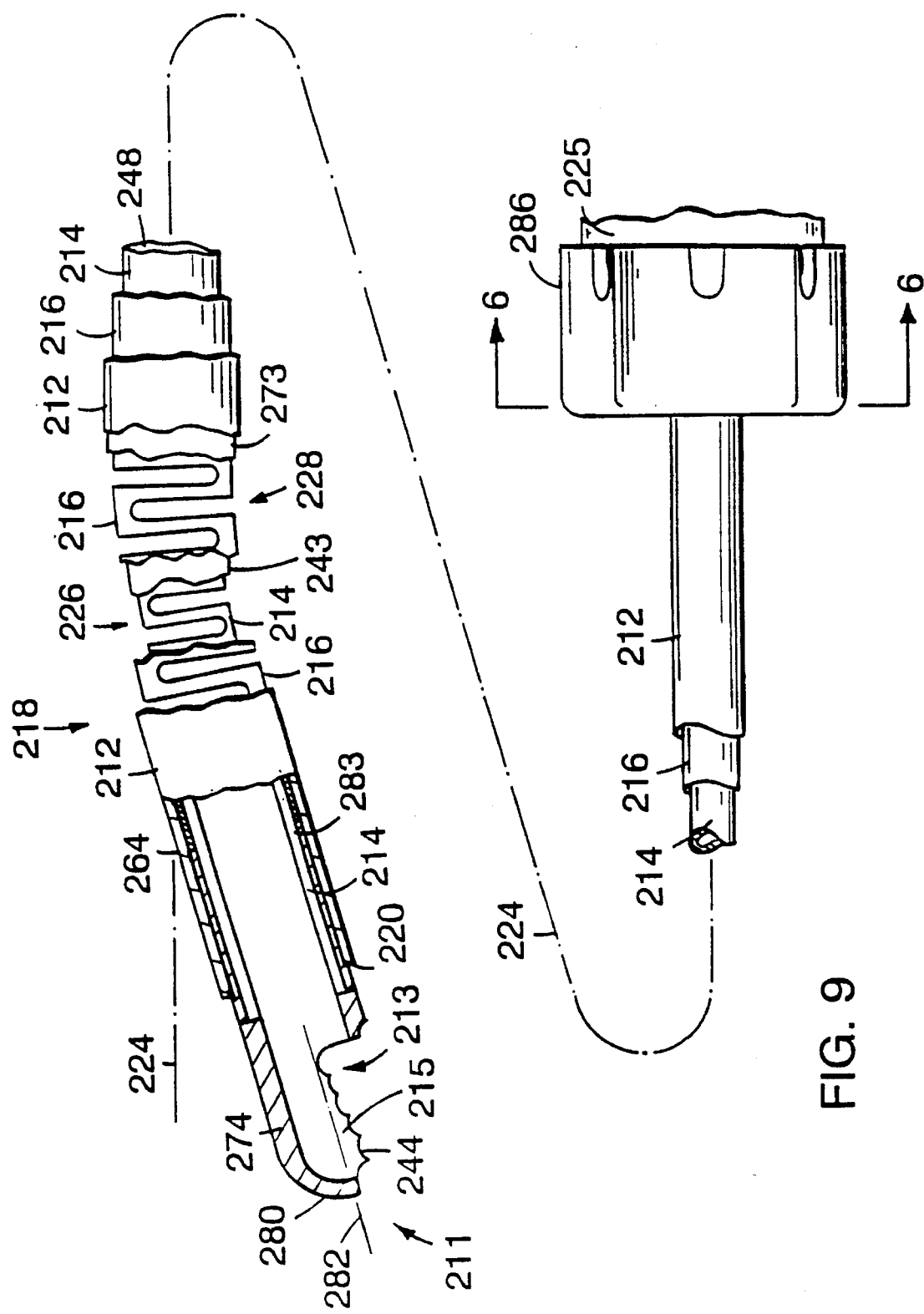
FIG. 9 is a partial cross-sectional view of portions of the instrument of FIG. 8, showing details of the tip and base.

A further embodiment of a surgical instrument in accordance with the invention is shown in FIGS. 8 and 9. Surgical instrument 210 includes a rigid outer tube 212, within which a surgical device is coaxially disposed. The surgical device, which carries a surgical tool 211 at its distal end, is comprised of a rotating, partially flexible inner tube 214, coaxially disposed within a partially flexible intermediate tube 216. Thus, whereas in the previously described embodiment the rigid member 16 was sandwiched between the two tubes 12, 14 comprising the surgical device, the surgical device of surgical instrument 210 is disposed coaxially within rigid outer tube 212.

The distal end of intermediate tube 216 includes an opening 213, the edges of which are sharpened and serrated, through which a cutting implement 215 (formed by sharpened, serrated edges of a similar opening in the distal end of inner tube 214) of surgical tool 211 is periodically exposed as inner tube 214 rotates. Outer tube 212 is curved through a bend region 218 disposed slightly proximally of the distal end 220 of outer tube 212 to offset surgical tool 211 angularly from a generally straight axis 224 of surgical instrument 210.

Tubes 212, 214, and 216 are proximally supported by a base 225 constructed of, e.g., polycarbonate plastic. As discussed in detail below, outer tube 212 mounts to a knob 286 of base 225, and intermediate tube 216 mounts to a hub 256 of base 225.

Inner tube 214 includes a slotted, flexible region 226 disposed within bend region 218 to accept the curvature imposed by bend region 218 and transmit torque (and other forces) applied at base 225 through bend region 218 to rotate cutting implement 215 with sufficient force to sever tissue or other body material exposed through opening 213. Intermediate tube 216 also has a slotted, flexible region 228 disposed within bend region 218 to accept the curvature imposed by bend region 218. (For clarity, in FIG. 9 inner tube 214 is not shown behind slotted, flexible region 228 of intermediate tube 216.) Flexible region 228 allows the relative rotational orientation between opening 213 and bend region 218 to be changed, without interfering with the ability of inner tube 214 to rotate within intermediate tube 216. As described in detail below, this feature enables the user to maintain surgical instrument 210 in an essentially fixed position, while rotationally varying the direction in which cutting is performed without changing the direction of offset of the bend region 218. Alternatively, the user can, without changing the direction in which cutting is performed, change the direction of offset of bend region 218.

Figure 10:
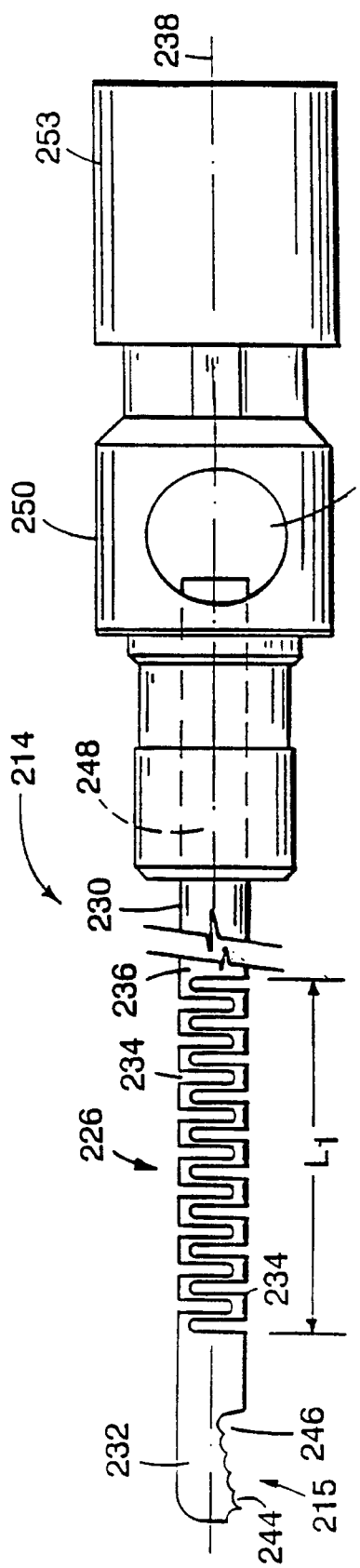

Referring also to FIG. 10, inner tube 214 is of generally the same construction as outer and inner tubes 12, 14 of the previously described embodiment. Rigid proximal and distal regions 230, 232 are connected by flexible region 226. Flexible region 226 is relieved with an axially extending series of circumferential slots 234 disposed in the walls 236 of tube 214, and is continuous with the adjacently disposed proximal and distal regions 230, 232. Each slot 234 is approximately 0.020 inches (0.508 mm) wide, and has a depth of about 0.135 inches (3.429 mm). The length $L_1$ of flexible region 226 should be sufficient (e.g. 0.70 inches, or 17.78 mm) that flexible region 226 spans the entire length of bend region 218.

A pliable sheath 243 (made from, e.g., heat-shrink tubing) slightly longer than $L_1$ is placed over inner tube 214 in bend region 218 to cover slots 234. (A portion of pliable sheath 243 in shown in FIG. 9.) Among other advantages, pliable sheath 43 helps prevent material from lodging within or passing through slots 234, and also helps prevent flexible region 226 from interfering with flexible region 228 as tubes 214, 216 rotate with respect to each other.

Distal region 232 of inner tube 214 supports cutting implement 215 (which is, for example, stainless steel and attached to tube 214 by welding or brazing). Cutting implement 215 is defined by serrated, sharpened edges 244 of a distal opening 246 in tube 214 and is sized to provide a close running fit with the interior surface of distal extension 274 of intermediate tube 216 (FIGS. 9 and 11) for efficient cutting. Opening 246 is an extension of a central aperture 248 in inner tube that runs the entire length of tube 214 (see also FIG. 9). After cutting implement 215 is attached to inner tube 214, the outer surface of the entire assembly is ground to a uniform outer diameter. Optionally, the outer surface of inner tube 214 may then be plated with silver to provide an improved friction surface between inner tube 214 and intermediate tube 216.

Proximal region 230 of inner tube 214 is mounted to a drive shaft 250 that rotates within base 225. Central aperture 248 terminates in a vacuum source opening 252 in drive shaft 250. The proximal end 253 of drive shaft 250 fits into a handpiece 310 (FIG. 14), which includes a motor 312 for rotating drive shaft 250 and inner tube 214 with respect to tubes 212 and 216. Opening 252 is coupled to a vacuum source 314 (FIG. 14) during operation to remove severed tissue and irrigating fluid from the surgical site via aperture 248 in a manner described in detail below.

Figure 11:
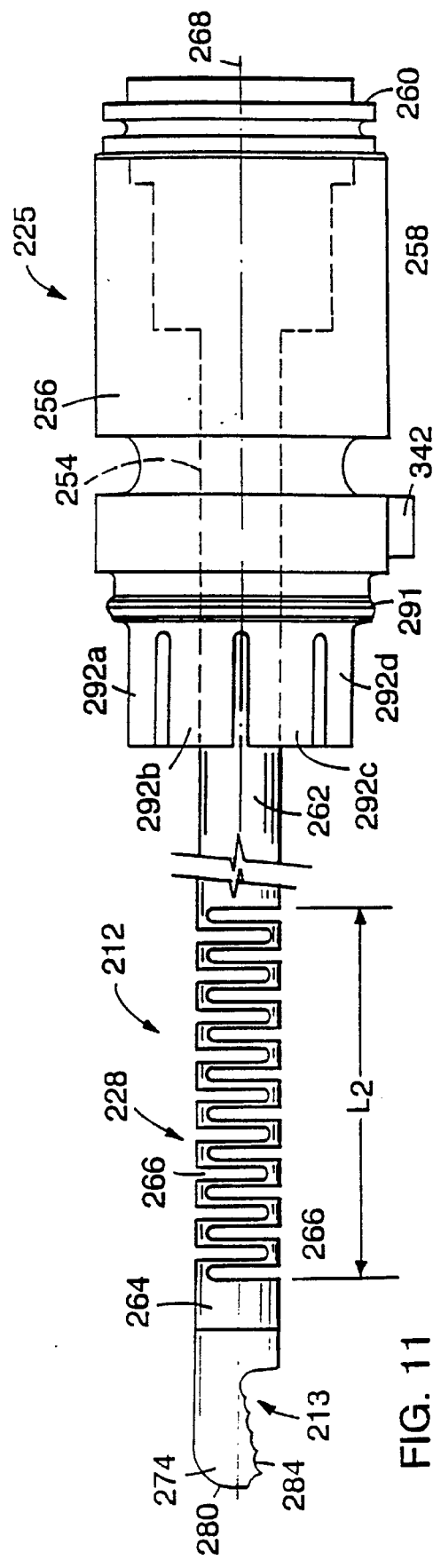

As shown in FIG. 11, intermediate tube 216 is hollow along its entire length to provide a passage 254 that receives inner tube 214 (FIG. 9). The proximal end of intermediate tube 216 is rigidly mounted, for example by ultrasonic welding, to a hub 256 of base 225. A cavity 258 in hub 256 communicates with passage 254 and is configured to receive drive shaft 250. During assembly, inner tube 214 is inserted through hub 256 into intermediate tube 216 (before bend region 218 is formed in outer tube 212). A pliable fitting 260 retains drive shaft 250 within hub 256. Fitting 260 further provides a fluid-tight seal when base 225 is inserted into handpiece 310.

Intermediate tube 216 is essentially a larger version of inner tube 214 and includes rigid proximal and distal regions 262, 264 that are integrally connected by flexible region 228. Flexible region 228 is relieved with an axially extending series of circumferential slots 266. Each slot 266 is approximately 0.025 inches (0.635 mm) wide and has a depth of about 0.140 inches (3.556 mm). The length $L_2$ of flexible region 228 should be sufficient (e.g. 0.70 inches, or 17.78 mm) that flexible region 228 spans the entire length of bend region 218. A pliable sheath 273 (made from, e.g., heat-shrink tubing) slightly longer than $L_2$ is placed over intermediate tube 216 in bend region 218 to cover slots 266. (A portion of pliable sheath 273 in shown in FIG. 9.)

To provide opening 213, a hollow, closed-ended distal extension 274 having the same outer diameter as intermediate tube 216 is secured to intermediate tube 216 at distal end 264. Extension 274 is, for example, stainless steel, and is welded or brazed to intermediate tube 216, which can be made of, for example, stainless steel.

Opening 213 is disposed in a distal tip 280 of extension 274 and faces somewhat to the side of intermediate tube 216. That is, opening 213 does not along its entire length extend completely to the centerline 282 of extension 274 (FIG. 9). As a result, while surgical tool 211 will cut tissue that enters opening 213 from the distal end of instrument 210, the majority of the cutting action is to one side. Moreover, the inner surface of tip 280 provides distal support for the rotating inner tube 214. The edges 284 of opening 213 are sharpened and serrated to cooperate with sharp edges 244 of cutting implement 215.

As shown in FIG. 9, when instrument 210 is assembled, a slight gap 283 exists between the outer diameter of inner tube 214 and the inner diameter of intermediate tube 216. The gap 283 accommodates the thickness of pliable sheath 243 covering flexible region 226. Extension 274, however, has a reduced inner diameter with respect to the remainder of intermediate tube 216, such that the clearance between cutting implement 215 and the inner diameter of extension 274 is small (e.g., approximately 0.002 inches, or 0.051 mm). This arrangement maintains the close-running fit between edges 244, 284 while allowing inner tube 214 to rotate freely. The essentially identical inner diameters of extension 274 and inner tube 214 avoid cutting implement 215 scoring or seizing as it rotates.

FIG. 12 shows the rigid member, outer tube 212 (before bend region 218 is formed), which is made from a rigid material such as metal (e.g., stainless steel). Proximal region 285 of outer tube 212 is rigidly secured, for example by ultrasonic welding, to a knob 286 at a sealed joint. A shoulder 289 on the inner surface of the proximal end of knob 286 engages a mating shoulder 291 on the outer surface of the distal end of hub 256 (FIG. 11), such that knob 286 rotatably mounts to hub 256 (see also FIG. 9). Thus, the relative rotational orientation between knob 286 and hub 256 can be changed, e.g., by grasping knob 286 and rotating hub 256, or by grasping hub 256 and rotating knob 286. The attachment mechanism connecting knob 286 and hub 256 is described in further detail below. Knob 286 is provided with a series of circumferentially spaced indentations 287 that facilitate the user's efforts manually to manipulate knob 286.

A central passage 288 extends through outer tube 212 and knob 286 to receive intermediate tube 216 and inner tube 214, which protrude through the open distal end 220 of outer tube 212. The inner diameter of outer tube 212 exceeds the outer diameter of intermediate tube 216 by a sufficient amount to accommodate pliable sheath 273 covering flexible region 228 (e.g., by approximately 0.005 inches, or 0.128 mm). This allows the user to change the relative rotational orientation between intermediate tube 216 and outer tube 212, but avoids excessive play or wobble between the intermediate and outer tubes 212, 216. After intermediate tube 216 is inserted into outer tube 212 and inner tube 214 is inserted into intermediate tube 216, outer tube 212 is curved to provide bend region 218 (FIG. 8).

When knob 286 is grasped firmly and hub 256 rotated, the rotational orientation of outer tube 212, and thus the direction of offset of bend region 218, remains fixed. Because proximal portion 262 of intermediate tube 216 is mounted to hub 256, rotating hub 256 also rotates intermediate tube 216 within outer tube 212. Intermediate tube 216 communicates this torque applied by the user at the base to extension 274 through flexible region 228 disposed in bend region 218. Thus, as hub 256 is rotated with respect to knob 286, the direction of offset of bend region 218 remains fixed, but opening 218 in extension 274 rotates with respect to bend region 218.

Alternatively, when hub 256 is grasped firmly and knob 288 is rotated, the directional orientation of opening 213 remains fixed (because hub 256 is also fixed), and the direction of offset of bend region 218 rotates (because knob 286 and outer tube 212 rotate). As the direction of offset of bend region 218 rotates, flexible region 228 allows the direction of offset of distal region 264 of intermediate tube 216 to rotate also.

Referring to FIGS. 11 and 13 (FIG. 13 for clarity does not show tubes 214 and 216 in cross-section), the interior of knob 286 is octagonal in cross-section, its inner surface being composed of eight flat surfaces 290a–h of equal width. Cantilevered from the distal end of hub 256 are eight distally projecting flexible fingers 292a–h spaced by equal amounts (i.e., 45°) around the circumference of shoulder 291. Fingers 292a–h lie perpendicular to longitudinal axis 268 of intermediate tube 216. Each of fingers 292a–h is an irregular pentagon in cross-section, such that when knob 286 is assembled onto hub 256, the radial outermost point 294a–h of each finger 292a–h rests in an apex formed by the intersection of adjacent flat surfaces 290a–h.

Fingers 292a–h and flat surfaces 290a–h coact to allow the relative rotational orientation between knob 286 and hub 256 to be changed, in a ratchet-like fashion, in discrete, 45° steps. As the relative rotational orientation changes (i.e., as the knob 286 and hub 256 rotate with respect to one another), outermost points 294a–h move across flat surfaces 290a–h, initially forcing fingers 292a–h radially inward. When outermost points 294a–h move past the respective midpoints of the surfaces 290a–h, the elastic energy stored in the displaced flexible fingers 292a–h forces the fingers radially outward until relative rotational orientation between knob 286 and hub 256 has changed by 45°, and fingers 292a–h rest in the adjacent apex. Thus, fingers 290a–h positively urge outermost points 294a–h into each associated apex as it is encountered, thereby giving the surgeon kinesthetic feedback as to the amount by which opening 213 has been rotated, and helping to avoid accidental rotation of outer tube 212 with respect to hub 256.

Figure 14:
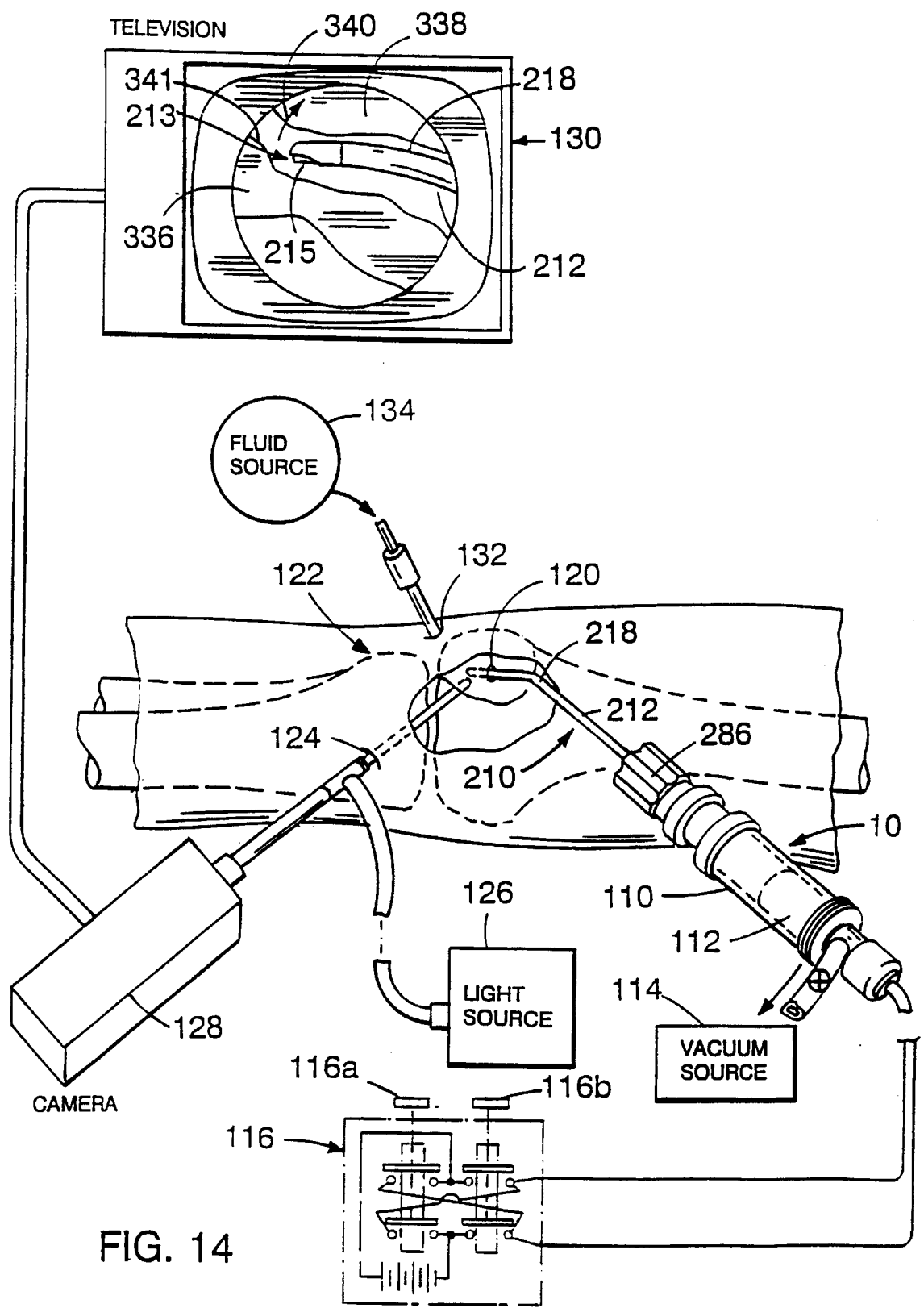
FIG. 14 shows the surgical instrument of FIG. 8 in use.

Referring also to FIG. 14, in operation surgical instrument 210 is employed similarly to surgical instrument 10, as described in connection with FIG. 7.

As described, fluid introduced through a third puncture wound 132 from a fluid source 134 distends the body joint and irrigates the site, rendering tissue 136 (which is, e.g., synovial tissue) mobile so that it floats and can be displaced (similar to the movement of seaweed in water). Note that synovial tissue 336 is located beneath outer tube 212; thus, the rotational orientation between knob 286 and hub 256 is selected to produce the desired orientation between the bend region 218 and opening 213 (FIGS. 9 and 13). The curvature provided by bend region 218 allows surgical instrument 210 to be easily positioned to place surgical tool 211 against tissue 336 (even if tissue 336 is located in a region of the joint that cannot easily be reached by a straight-shafted instrument) without manipulating instrument 210 unduly or requiring that additional punctures be made to gain access to tissue 336. This reduces patient discomfort, as well as the chances for infection and other deleterious consequences of the surgery.

The surgeon progressively cuts away synovial tissue 336 by moving surgical instrument 210 from side to side and in the axial direction using handpiece 310 (while viewing television screen 130). If during the procedure the surgeon wishes to cut tissue from another region of the synovial tissue, the present invention allows him to do so simply by changing the relative rotational orientation between surgical tool opening 213 and bend region 218.

For example, if the surgeon wishes to remove tissue from region 338 located above outer tube 212 (e.g., in the direction of arrow 340), he grasps knob 286 with the finger and thumb of one hand and turns handpiece 110, which in turn rotates hub 256. Handpiece 110 is provided with a distinct protuberance (not shown) that points in the same direction as tab 342 on hub 256 (FIG. 11) and opening 213 in surgical tool 211. Thus, the surgeon would continue to grasp knob 286 and rotate handpiece 110 until he tactually senses from the handpiece protuberance that opening 213 is properly oriented. The rotational force applied by the surgeon is transmitted through bend region 218 by flexible region 228, thereby causing distal extension 274 of intermediate tube 216 to rotate with respect to outer tube 212, changing the rotational orientation of opening 213 with respect to bend region 218 (in this case, by 180°).

Alternatively, if for example the surgeon wishes to change the direction of offset of bend region 218 without changing the direction of opening 213 (and thus the cutting direction of surgical tool 211), e.g. to remove tissue from region 341, he grasps handpiece 110 and rotates knob 286 with the finger and thumb of one hand. When the direction of offset of bend region 218 is as desired (in this case, when it had been rotated by 180°), the surgeon then moves the entire instrument axially until opening 213 was adjacent to region 341.

The surgeon can change the relative rotational orientation between bend region 218 and opening 213 at any time. For example, inner tube 214 can be driven by motor 112 or may be stationary while the surgeon rotates opening 213. Distal extension 274 rotates smoothly with respect to the stationary outer tube 212, while providing constant distal support (at tip 280) for rotating inner tube 214. The surgeon can return to cutting tissue 336 at any time simply by rotating handpiece 310 in either direction while holding knob 286 fixed (if the surgeon had been cutting from region 338), or by rotating knob 286 in either direction while holding handpiece 110 fixed (if the surgeon had been cutting from region 341).

Tissue fragments and other body material cut by surgical tool 211 are withdrawn from the surgical site along with irrigation fluid via central aperture 248 of inner tube 214 (FIG. 9) in response to suction applied by vacuum source 114. Flexible sheath 243 covering inner tube 214 ensures that tissue fragments, irrigation fluid, and other material do not pass through slots 234, thereby assisting in the transport of tissue fragments through the chamber and out of surgical instrument 210.

Although surgical instrument 210 is shown with opening 213 aligned in the same direction as tab 342 on hub 256 (FIG. 11), it is readily apparent that other alignments (e.g., in the opposite direction, to the right or left, or anywhere in between these directions) are possible. Indeed, a set of surgical instruments may be provided, each with a different opening 213 orientation, to give the user maximum flexibility in determining the optimum configuration for a given surgical procedure. In addition, outer tube 212 can be curved to any desired degree.

Surgical tools other than the cutting implement shown in the figures can be used. For example, the surgical tool can be configured to cut tissue exposed to distal tip 280 of intermediate tube 216. In this end cutter embodiment, coacting cutting edges are provided at the distal tips of both the inner and the intermediate tubes, and an axial bearing maintains the respective edges in close cutting relationship. Further, axial force can be used instead of, or in addition to, torque to operate the surgical tool. For example, the surgical tool could be a hinged punch or jaw assembly operated by an axial force applied at hub 256.

While the invention has been described in terms of surgical instruments for arthroscopy, the invention may also be used with other types of instruments, for example, instruments configured for other kinds of endoscopic procedures and for biopsy applications.

What is claimed is:

1. A surgical instrument disposed generally along an axis, said surgical instrument comprising a first member that extends distally from a base and has an opening in a distal region thereof for admitting tissue, said first member including a bend region that angularly offsets said distal region of said first member from said axis so that said distal region is aligned with a distal axis, a second member for moving a cutting implement and causing it to cut tissue that is exposed to said implement through said opening, and a rotator coupled to said first member for rotating said first member with respect to said base to rotate said opening around to said distal axis, said distal axis and said distal region remaining aligned as said first member rotates with respect to said base.

2. The instrument of claim 1 wherein said rotator allows said rotational orientation of said opening to be changed over a range of at least 180°.

3. The instrument of claim 2 wherein said rotator allows said rotational orientation of said opening to be changed over a range of 360°.

4. The instrument of claim 3 wherein said rotator is configured to be manually actuated by a user of said instrument to change said rotational orientation of said opening.

5. The instrument of claim 4 wherein said rotator includes a knob that is rigidly secured to a proximal end of said first member and rotatably mounted to a stationary portion of said base.

6. The instrument of claim 5 wherein said knob is mounted to said stationary portion so that said knob can be selectively rotated to a plurality of discrete positions, thereby to allow said opening to be selectively positioned to a corresponding plurality of discrete rotational orientations.

7. The instrument of claim 6 wherein said stationary portion includes a plurality of recesses each of which corresponds to one of said discrete positions, said knob including a plunger for selectively engaging said recesses, to maintain said opening in the corresponding discrete rotational orientation.

8. The instrument of claim 7 wherein said knob is resiliently biased toward said stationary portion to retain said plunger in a said recess, thereby to avoid accidental rotation of said first member with respect to said base.

9. The instrument of claim 8 wherein said second member has a proximal end that is secured to a drive shaft mounted for movement with respect to said stationary portion and said knob.

10. The instrument of claim 9 wherein said drive shaft is adapted to be driven by a motor to rotate said second member with respect to said first member and move said cutting implement.

11. The instrument of claim 10 wherein said second member is hollow and is adapted receive suction at its proximal end and to transport body material cut by said cutting implement away from a surgical site while the instrument remains in situ for further cutting.

12. The instrument of claim 11 wherein said cutting implement comprises a blade.

13. A surgical instrument disposed generally along an axis, said surgical instrument comprising
a first member that extends distally from a base and has an opening in a distal region thereof for admitting tissue, said first member including a bend region that angularly offsets a distal region of said first member from said axis in a selected direction,
a rotator coupled to said first member for rotating said first member with respect to said base to selectively change a rotational orientation of said opening with respect to said axis,
said first member being relatively flexible at least in said bend region to allow said rotator to change said rotational orientation of said opening without changing said selected direction of said offset,
a second member for moving a cutting implement and causing it to cut tissue that is exposed to said implement through said opening, and
at least a portion of said second member being axially aligned with said bend region, said portion being relatively flexible to transmit force applied at a proximal end thereof through said bend region to move said cutting implement.

14. The instrument of claim 13 wherein said first member is relieved in said bend region to provide the relative flexibility.

15. The instrument of claim 13 wherein said proximal region and said distal region of said first member are rigid, said first member being relieved in said bend region to provide the relative flexibility.

16. The instrument of claim 14 or 15 wherein said first member is relieved with a plurality of discrete openings disposed in walls thereof.

17. The instrument of claim 16 wherein said openings comprise a series of axially spaced, circumferentially extending slots.

18. The instrument of claim 17 wherein said slots extend radially into said first member over approximately 75% of the diameter of said first member.

19. The instrument of claim 17 wherein adjacent ones of said slots extend into said first member from opposite directions.

20. The instrument of claim 13 wherein said second member is disposed within said first member and wherein said proximal end of said second member and a distal end of said second member are rigid, said portion of said second member that is disposed in said bend region being relieved to provide the relative flexibility.

21. The instrument of claim 20 wherein said portion of said second member is relieved with a series of axially spaced, circumferentially extending slots.

22. The instrument of claim 21 further comprising pliable material disposed in at least some of said slots.

23. The instrument of claim 22 wherein said force is applied by a motor that applies torque to said proximal end of said second member, said relieved portion of said second member being configured to transmit said torque through said bend region to said cutting implement.

24. The instrument of claim 23 wherein said means for providing said bend region includes a rigid member that is disposed coaxially with said first member and said second member and is curved in said bend region.

25. The instrument of claim 24 wherein said first member and said second member are each relieved with a plurality of openings in said bend region to provide said flexibility and said second member moves with respect to said first member to move said cutting implement, said rigid member radially separating said first member and said second member at least in said bend region to avoid interference therebetween as said second member moves.

26. The instrument of claim 25 wherein said second member is disposed within said rigid member and said rigid member is disposed within said first member.

27. The instrument of claim 26 wherein said rigid member has an open distal tip disposed proximally of said cutting implement and opening, said first member and said second member being configured to contact each other distally of said tip to maintain said cutting implement in tissue cutting relationship with edges of said opening.

28. The instrument of claim 27 wherein a portion of said distal region of said first member has a reduced inner diameter relative to other portions of said first member to provide said contact with said second member.

29. The instrument of claim 28 wherein said portion of said distal region of said first member abuts said tip of said rigid member, and said inner diameter is the same as an inner diameter of said rigid member.

30. The instrument of claim 29 wherein at least said first member is relieved with a plurality of openings in said bend region to provide said flexibility, and further comprising a pliable sheath disposed over said first member in said bend region that covers said openings.

31. A surgical instrument disposed generally along an axis, said surgical device comprising a first member that extends distally from a base and has an opening in a distal region thereof for admitting tissue, means for providing said first member with a bend region that angularly offsets said distal region from said axis in a selected direction, a second member disposed within said first member, for transmitting force applied to a proximal end thereof to move a cutting implement disposed at a distal end thereof and cause it to cut tissue that is exposed to said implement through said opening, at least a portion of said second member that is disposed within said bend region being relatively flexible, means for rotating said first member with respect to said base, said first member being relatively flexible at least in said bend region to transmit said rotation through said bend region to selectively change a rotational orientation of said opening with respect to said axis without changing said selected direction of said offset.

32. The instrument of claim 31 wherein said first member is relieved in said bend region with a plurality of discrete openings disposed in walls thereof to provide the relative flexibility.

33. The instrument of claim 31 wherein said portion of said second member is relieved with a plurality of discrete openings disposed in walls thereof to provide the relative flexibility.

34. The instrument of claim 33 wherein said force is applied by a motor that applies torque to proximal end of said second member, said portion of said second member being configured to transmit said torque through said bend region to said cutting implement.

35. The instrument of claim 34 wherein said means for providing said bend region includes a rigid member that is disposed coaxially with said first member and said second member and is curved in said bend region.

36. The instrument of claim 35 wherein said first member and said second member are each relieved with a plurality of openings in said bend region to provide said flexibility and said second member rotates with respect to said first member to move said cutting implement, said rigid member radially separating said first member and said second member at least in said bend region to avoid interference therebetween as said second member rotates.

37. The instrument of claim 36 wherein said second member is disposed within said rigid member and said rigid member is disposed within said first member.

38. The instrument of claim 37 wherein said means for rotating is configured to be manually actuated by a user of said instrument to change said rotational orientation of said opening.

39. The instrument of claim 38 wherein said means for rotating includes a knob that is rigidly secured to a proximal end of said first member and rotatably mounted to a stationary portion of said base.

40. The instrument of claim 39 wherein said knob is mounted to said stationary portion so that said knob can be selectively rotated to a plurality of discrete positions, thereby to allow said opening to be selectively positioned to a corresponding plurality of discrete rotational orientations.

41. A surgical instrument disposed generally along an axis, said surgical device comprising an outer tube that extends distally from a base and has an opening in a distal region thereof for admitting tissue, a stationary support tube that extends distally from a base and is disposed within said outer tube, said support tube including a bend region disposed between said base and said distal region to angularly offset said distal region from said axis in a selected direction, an inner tube disposed within said support tube for transmitting force applied to a proximal end thereof to move a cutting implement disposed at a distal end thereof and cause it to cut tissue that is exposed to said implement through said opening, at least a portion of said inner tube that is disposed within said bend region being relatively flexible, and means for rotating said outer tube with respect to said base about said stationary support tube, said outer tube being relatively flexible at least in said bend region to transmit said rotation through said bend region to selectively change a rotational orientation of said opening with respect to said axis without changing said selected direction of said offset.

42. The instrument of claim 41 wherein said outer tube and said inner tube are each relieved in said bend region to provide the relative flexibility.

43. The instrument of claim 42 wherein said outer tube and said inner tube are each relieved with a plurality of discrete openings disposed in walls thereof.

44. The instrument of claim 43 wherein said force is applied by a motor that applies torque to said proximal end of said inner tube, said portion of said second member being relieved to provide the relative flexibility and being configured to transmit said torque through said bend region to said cutting implement.

45. The instrument of claim 44 wherein said support tube has an open distal tip disposed proximally of said cutting implement and opening, said outer tube and said inner tube being configured contact each other distally of said tip to maintain said cutting implement in tissue cutting relationship with edges of said opening.

46. The instrument of claim 45 wherein a portion of said distal region of said outer tube has a reduced inner diameter relative to other portions of said outer tube to provide said contact with said inner tube.

47. The instrument of claim 46 wherein said portion of said distal region of said outer tube abuts said tip of said support tube, and said inner diameter is the same as an inner diameter of said support tube.

48. The instrument of claim 47 wherein said means for rotating is configured to be manually actuated by a user of said instrument to change said rotational orientation of said opening.

49. The instrument of claim 48 wherein said means for rotating includes a knob that is rigidly secured to a proximal end of said outer tube and rotatably mounted to a stationary portion of said base.

50. The instrument of claim 49 wherein said knob is mounted to said stationary portion so that said knob can be selectively rotated to a plurality of discrete positions, thereby to allow said opening to be selectively positioned to a corresponding plurality of discrete rotational orientations.

51. A surgical instrument comprising a base having a first section and a second section rotatably coupled thereto, a rigid member having a proximal region mounted to said first section of said base and a bend region that angularly offsets a distal region of said rigid member from said proximal region, a surgical device extending distally from said second section of said base coaxially with said rigid member, said second section inducing a corresponding rotation of said surgical device with respect to said rigid member when said second section is rotated with respect to said first section, said surgical device being coupled to a surgical tool disposed distally of said bend region at a selected rotational orientation with respect to said bend region, said surgical tool being configured to manipulate body tissue in an area adjacent to said surgical tool, an orientation of said area with respect to said bend region being determined by said rotational orientation of said surgical tool, said surgical device being configured to independently: (1) transmit a force applied at a proximal end of said surgical device through said bend region to operate said surgical tool to manipulate body tissue in said area, and (2) transmit the rotation of said surgical device induced by said second section of said base through said bend region to change said selected rotational orientation of said surgical tool with respect to said bend region to change said orientation of said area with respect to said bend region.

52. The instrument of claim 51 wherein said relative rotational orientation between said surgical tool and said bend region can be changed over a range of at least 360°.

53. The instrument of claim 52 wherein said relative rotational orientation between said surgical tool and said bend region can be changed manually by a user of said instrument.

54. The instrument of claim 53 wherein said first section of said base can be selectively rotated to a plurality of discrete positions with respect to said second section of said base, thereby to allow said relative rotational orientation between said surgical tool and said bend region to be selectively changed to a corresponding plurality of discrete relative rotational orientations.

55. The instrument of claim 54 wherein said second section further includes a plurality of flexible cantilevered fingers each of which corresponds to one of said discrete positions, said first section further including a plurality of mating regions, each of said mating regions engaging one of said fingers to maintain said discrete relative rotational orientation between said surgical tool and said bend region.

56. The instrument of claim 51 wherein said surgical device is relatively flexible at least in said bend region.

57. A surgical instrument comprising a base having a first section and a second section rotatably coupled thereto, a rigid member having a proximal region mounted to said first section of said base and a bend region that angularly offsets a distal region of said rigid member from said proximal region, a surgical device extending distally from said second section of said base coaxially with said rigid member, said surgical device comprising a first member coaxially disposed within a second member, said second member being mounted to said second section of said base so that said second section induces a corresponding rotation of said second member with respect to said rigid member when said second section is rotated with respect to said first section, said first and said second members of said surgical device being coupled to a surgical tool disposed distally of said bend region at a selected rotational orientation with respect to said bend region, said first member being relatively flexible at least in said bend region to transmit a force applied at a proximal end of said first member through said bend region to operate said surgical tool to manipulate body tissue adjacent thereto, said first member being movable with respect to said second member in response to said force, and said second member being relatively flexible at least in said bend region to transmit the rotation of said second member induced by said second portion of said base through said bend region to change said selected rotational orientation of said surgical tool with respect to said bend region.

58. The instrument of claim 57 wherein said second member is coaxially disposed within said rigid member.

59. The instrument of claim 58 wherein said rigid member is coaxially disposed within said second member and said first member is coaxially disposed within said rigid member.

60. The instrument of claim 57 wherein said second member and said first member are both relieved to render them relatively flexible.

61. The instrument of claim 60 wherein said second member and said first member are both relieved with a series of axially spaced, circumferentially extending slots.

62. The instrument of claim 61 further including a first pliable sheath disposed to cover said slots of said first member, and a second pliable sheath disposed to cover said slots of said second member.

63. The instrument of claim 62 wherein said first member is hollow and is adapted to receive suction at its proximal end and to transport body material cut by said surgical tool away from a surgical site while the instrument remains in situ for further cutting.

64. The instrument of claim 63 wherein said surgical tool comprises a first opening in a distal region of said first member and a second opening in a distal region of said second member, an edge of said first opening being arranged to move toward and closely past an edge of said second opening in response to said force to cut tissue entering through said first and said second openings.

65. The instrument of claim 64 wherein said force is a torque applied by a motor coupled to a proximal end of said first member, said relatively flexible first member being configured to transmit said torque through said bend region to move said edge of said first opening with respect to said second opening.

66. A surgical instrument comprising an outer rigid tube having a proximal region mounted to a first section of a base and a bend region that angularly offsets a distal region of said outer tube from said proximal region, an intermediate tube having a proximal end mounted to a second section of said base, said second section of said base being rotatably mounted with respect to said first section of said base and said intermediate tube being disposed coaxially within said outer tube and carrying a first portion of a surgical tool distal of said bend region, said intermediate tube having a relatively flexible region at least in said bend region to transmit force applied at said second section of said base through said bend region to change a relative rotational orientation between said first portion of said surgical tool and said bend region, an inner tube disposed coaxially within said intermediate tube, said inner tube carrying a second portion of said surgical tool distal of said bend region and having a relatively flexible region at least in said bend region to transmit force applied at a proximal end of said inner tube through said bend region to move said second portion of said surgical tool with respect to said first portion of said surgical tool.

67. The instrument of claim 66 wherein said inner tube and said intermediate tube are both relieved in said relatively flexible region.

68. The instrument of claim 67 wherein said inner tube and said intermediate tube are both relieved with a series of axially spaced, circumferentially extending slots.

69. The instrument of claim 68 further including a first pliable sheath disposed to cover said slots of said inner tube, and a second pliable sheath disposed to cover said slots of said intermediate tube.

70. The instrument of claim 69 wherein said first portion of said surgical tool comprises a first opening in a distal region of said intermediate tube and said second portion of said surgical tool comprises a second opening in a distal region of said inner tube, an edge of said second opening being arranged to move toward and closely past an edge of said first opening to cut tissue entering through said first and second openings in response to force applied at said proximal end of said inner tube.

71. The instrument of claim 70 wherein said inner tube is hollow and is adapted to receive suction at its proximal end and to transport body material cut by said surgical tool away from a surgical site while the instrument remains in situ for further cutting.

72. The instrument of claim 71 wherein said first section of said base can be selectively rotated to a plurality of discrete positions with respect to said second section of said base, thereby to allow said relative rotational orientation between said first portion of said surgical tool and said bend region to be selectively changed to a corresponding plurality of discrete relative rotational orientations.

73. The instrument of claim 72 wherein said second section further includes a plurality of flexible cantilevered fingers each of which corresponds to one of said discrete positions, said first section further including a plurality of mating regions, each of said mating regions engaging one of said fingers to maintain said discrete relative rotational orientation between said first portion of said surgical tool and said bend region.

74. A method of surgery for a joint space comprising
introducing into said joint from outside said joint via a puncture wound in the flesh:
a first conduit for introducing fluid from a fluid source,
a visualization instrument, and
a surgical instrument comprising
a base having a first section and a second section rotatably coupled thereto,
a rigid member having a proximal region mounted to said first section of said base and a bend region that angularly offsets a distal region of said rigid member from said proximal region,
a surgical device extending distally from said second section of said base coaxially with said rigid member, said second section inducing a corresponding rotation of said surgical device with respect to said rigid member when said second section is rotated with respect to said first section,
said surgical device being coupled to a surgical tool disposed distally of said bend region at a selected rotational orientation with respect to said bend region, said surgical tool being configured to manipulate body tissue in an area adjacent to said surgical tool, an orientation of said area with respect to said bend region being determined by said rotational orientation of said surgical tool, said surgical device being configured to independently: (1) transmit a force applied at a proximal end of said surgical device through said bend region to operate said surgical tool to manipulate body tissue in said area, and (2) transmit the rotation of said surgical device induced by said second portion of said base through said bend region to change said selected rotational orientation of said surgical tool with respect to said bend region to change said orientation of said area with respect to said bend region;

introducing fluid through said first conduit into said joint to distend said joint and to provide a clear field for viewing through said visualization instrument, positioning said visualization instrument to enable observation of a first area of said joint to be surgically treated, on the basis of said visual observation, positioning said surgical instrument adjacent to said first area of said joint and applying said force at said proximal end of said surgical device to operate said surgical tool to manipulate body tissue in said first area of said joint, rotating said second section of said base with respect to said first section to change said selected rotational orientation of said surgical tool with respect to said bend region, and positioning said surgical instrument adjacent to a second area of said joint and applying said force to operate said surgical tool to manipulate body tissue in said second area, said second area having a different rotational orientation with respect to said bend region than said first area.

* * * * *

UNITED STATES PATENT AND TRADEMARK OFFICE
CERTIFICATE OF CORRECTION

PATENT NO. : 5,620,447  
DATED : April 15, 1997  
INVENTOR(S) : Graham Smith et al.

Page 1 of 2

It is certified that error appears in the above-identified patent and that said Letters Patent is hereby corrected as shown below:

Col. 16, claim 1, line 65, delete "to".

Col. 17, claim 4, line 7, replace "3" with --1--.

Col. 17, claim 9, line 29, replace "8" with --5--.

Col. 17, claim 11, line 37, replace "10" with --1--.

Col. 17, claim 12, line 42, replace "11" with --1--.

Col. 18, claim 23, line 31, replace "22" with --20--.

Col. 18, claim 24, line 36, replace "23" with --13--.

Col. 18, claim 26, line 48, replace "25" with --24--.

Col. 18, claim 30, line 65, replace "29" with --26--.

Col. 19, claim 34, line 31, replace "33" with --32--.

Col. 19, claim 35, line 36, replace "34" with --31--.

Col. 19, claim 37, line 48, replace "36" with --35--.

Col. 19, claim 38, line 51, replace "37" with --31--.

Col. 20, claim 44, line 26, replace "43" with --41--.

UNITED STATES PATENT AND TRADEMARK OFFICE
CERTIFICATE OF CORRECTION

PATENT NO. : 5,620,447
DATED : April 15, 1997
INVENTOR(S) : Graham Smith et al.

It is certified that error appears in the above-identified patent and that said Letters Patent is hereby corrected as shown below:

Col. 20, claim 45, line 32, replace "44" with --41--.

Col. 20, claim 48, line 46, replace "47" with --41--.

Col. 21, claim 53, line 25, replace "52" with --51--.

Col. 21, claim 54, line 29, replace "53" with --51--.

Col. 22, claim 59, line 13, replace "58" with --53--.

Col. 22, claim 63, line 25, replace "62" with --57--.

Col. 22, claim 64, line 29, replace "63" with --57--.

Col. 23, claim 70, line 11, replace "69" with --66--.

Col. 23, claim 71, line 20, replace "70" with --66--.

Col. 23, claim 72, line 25, replace "71" with --66--.

Signed and Sealed this

Thirteenth Day of July, 1999

Attest:

Attesting Officer

Q. TODD DICKINSON

Acting Commissioner of Patents and Trademarks